(12) United States Patent
Rice et al.

(10) Patent No.: US 7,816,334 B2
(45) Date of Patent: Oct. 19, 2010

(54) MATERIALS AND METHODS RELATING TO IMMUNE RESPONSES TO FUSION PROTEINS

(75) Inventors: Jason Rice, Southampton (GB); Freda Stevenson, Southampton (GB)

(73) Assignee: Cancer Research Technology Limited, London (GB)

( * ) Notice: Subject to any disclaimer, the term of this patent is extended or adjusted under 35 U.S.C. 154(b) by 1345 days.

(21) Appl. No.: 10/257,657

(22) PCT Filed: Apr. 17, 2001

(86) PCT No.: PCT/GB01/01719

§ 371 (c)(1), (2), (4) Date: Mar. 27, 2003

(87) PCT Pub. No.: WO01/79510

PCT Pub. Date: Oct. 25, 2001

(65) Prior Publication Data

US 2003/0158136 A1     Aug. 21, 2003

(30) Foreign Application Priority Data

Apr. 17, 2000  (GB) ................. 0009470.6

(51) Int. Cl.
*A61K 31/70* (2006.01)
*C12N 15/63* (2006.01)
*C07H 21/04* (2006.01)
*C12Q 1/68* (2006.01)

(52) U.S. Cl. ............... 514/44; 435/455; 536/23.4

(58) Field of Classification Search ............ None
See application file for complete search history.

(56) References Cited

U.S. PATENT DOCUMENTS 6,228,621 B1 * 5/2001 Williams et al. ........... 435/69.7
6,534,482 B1 * 3/2003 Fikes et al. .................. 514/44
6,936,464 B1 * 8/2005 Zhu et al. .................. 435/320.1

FOREIGN PATENT DOCUMENTS

WO     WO 99/15671     4/1999

OTHER PUBLICATIONS

Rice et al. DNA fusion vaccine designed to induce cytotoxic T cell responses against defined peptide motifs: Implications for cancer vaccines. J. Immunology 167:1558-1565, 2001.*
Rice et al. Manipulation of pathogen-derived genes to influence antigen presentation via DNA vaccines. Vaccine 17:3030-3038, 1999.*
Fairweather et al. Cloning, nucelotide sequencing, and expressionof Tetanus Toxin Fragment C in *Escherichia coli.* J. Bacteriology 165:21-27, 1986.*
Panina-Bordignon et al. Universally immunogenic T cell epitopes: promiscuous binding to human MHC class II and promiscuous recognition by T cells. Eur. J. Immunol. 19:2237-2242, 1989.*
Spellenberg, M.B., "DNA vaccines against lymphoma," Journal of Immunology, 159:1885-1892, (1997).
Valmori, D., et al., "Use of human universally antigenic tetanus toxin T cell epitopes as carriers for human vaccination," Journal of Immunology, 149:717-721, (1992).
King, C.A., et al., "DNA vaccines with single-chain Fv fused to fragment C of tetanus toxi induce protective immunity against . . . ," Nature Medicine, 4:1281-1286, (1998).
Herreros, J., et al., "C-terminal half of tetanus toxin fragment C is sufficient for neuronal binding and interaction with a . . . ," Biochemical Journal, 347:199-204, (2000).
Umland, T.C., et al., "Structure of the receptor binding fragment Hc of tetanus neurotoxin," Nature Structural Biology, 4:788-792, (1997).

* cited by examiner

*Primary Examiner*—Quang Nguyen
(74) *Attorney, Agent, or Firm*—Dann, Dorfman, Herrell & Skillman; Robert C. Netter, Jr.

(57) ABSTRACT

The invention provides nucleic acid construct and nucleic acid expression vectors directing the expression of a fusion protein consisting of a disease peptide antigen and a first domain of FrC of tetanus toxin. The invention provides nucleic acid (DNA) vaccines for use in inducing an immune response against a disease. There is also provided methods of producing nucleic acid constructs and vectors for use as nucleic acid (DNA) vaccines.

42 Claims, 18 Drawing Sheets

Figure 1:
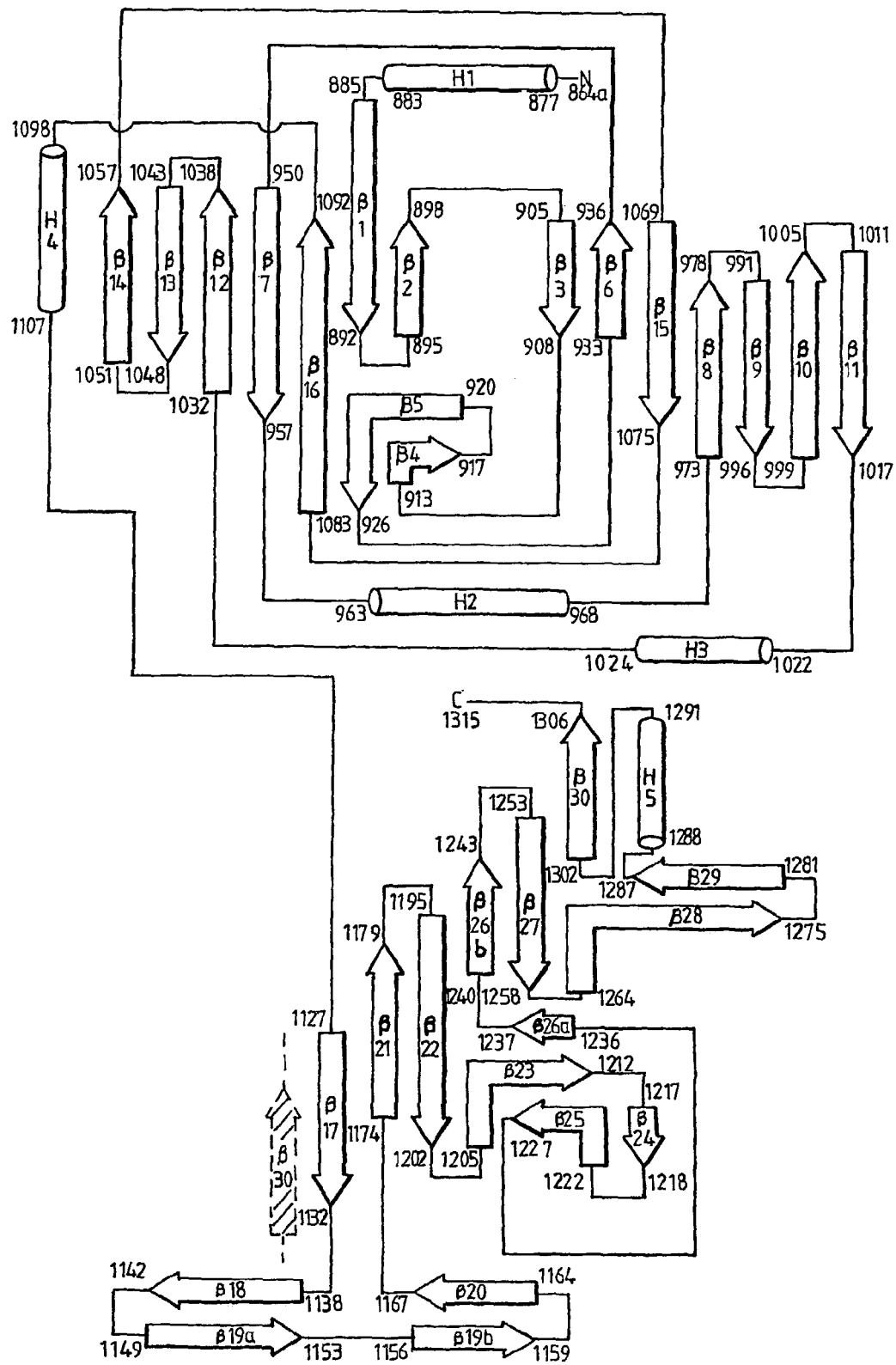
Figure 2:
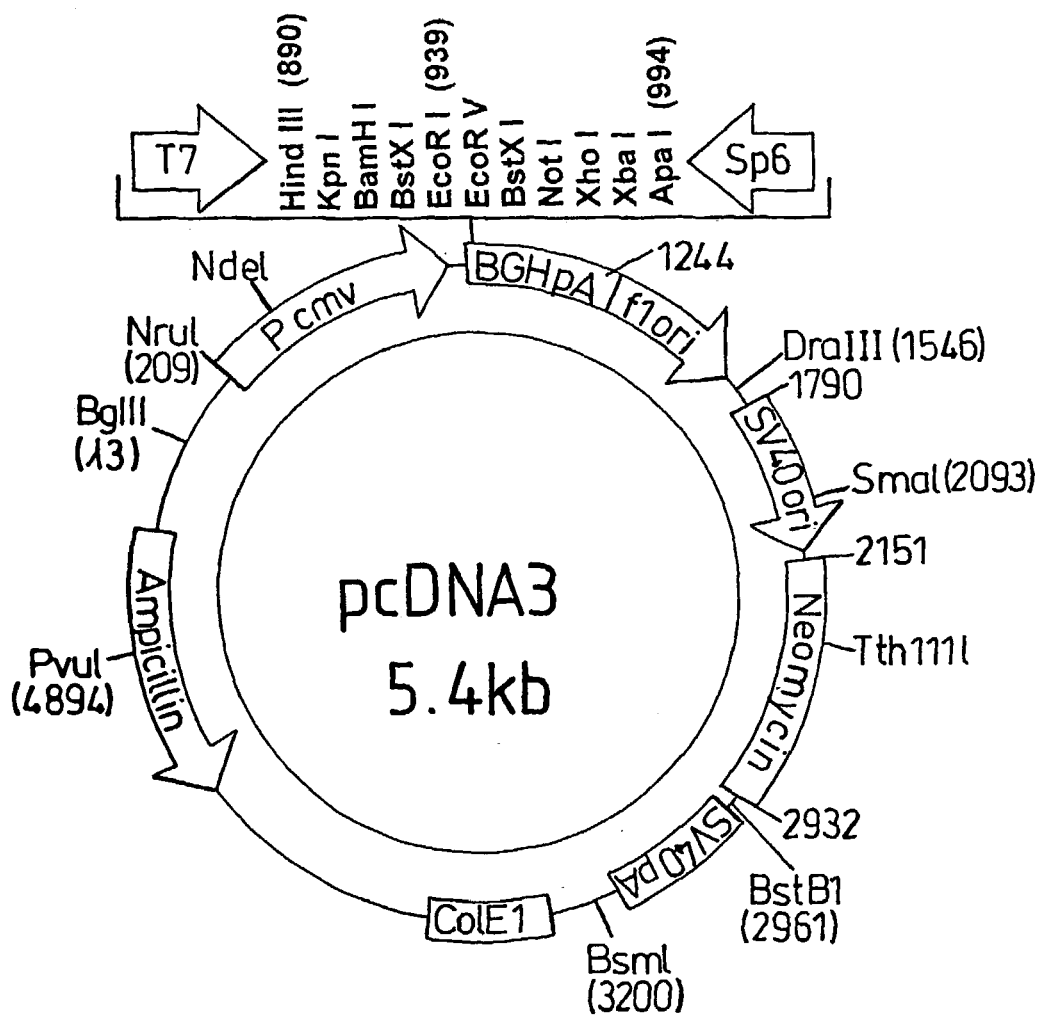

CMV promoter: bases 209-863
T7 promoter: bases 864-882
Polylinker: bases 889-994
Sp6 promoter: bases 999-1016
BGH poly A: bases 1018-1249
SV40 promoter: bases 1790-2115
SV40 origin of replication: bases 1984-2069
Neo$^R$ORF: bases 2151-2932
SV40 poly A: bases 3120-3250
pUC19 backbone: bases 3272-5446
Amp$^R$ORF: bases 4450-5310

```
          |    10   |    20   |    30   |    40   |    50   |
   1 GACGGATCGG GAGATCTCCC GATCCCCTAT GGTCGACTCT CAGTACAATC
  51 TGCTCTGATG CCGCATAGTT AAGCCAGTAT CTGCTCCCTG CTTGTGTGTT
 101 GGAGGTCGCT GAGTAGTGCG CGAGCAAAAT TTAAGCTACA ACAAGGCAAG
 151 GCTTGACCGA CAATTGCATG AAGAATCTGC TTAGGGTTAG GCGTTTTGCG
 201 CTGCTTCGCG ATGTACGGGC CAGATATACG CGTATCTGAG GGGACTAGGG
 251 TGTGTTTAGG CGAAAAGCGG GGCTTCGGTT GTACGCGGTT AGGAGTCCCC
 301 TCAGGATATA GTAGTTTCGC TTTTGCATAG GGAGGGGGAA ATGTAGTCTT
 351 ATGCAATACA CTTGTAGTCT TGCAACATGG TAACGATGAG TTAGCAACAT
 401 GCCTTACAAG GAGAGAAAAA GCACCGTGCA TGCCGATTGG TGGAAGTAAG
 451 GTGGTACGAT CGTGCCTTAT TAGGAAGGCA ACAGACAGGT CTGACATGGA
 501 TTGGACGAAC CACTGAATTC CGCATTGCAG AGATAATTGT ATTTAAGTGC
 551 CTAGCTCGAT ACAATAAACG CCATTTGACC ATTCACCACA TTGGTGTGCA
 601 cctccaagct tagcatggac tggacctgga gggtcttctg cttgctggct
 651 gtggccccgg gggcccactc ccaggtgcag ctgcaggtcg acctcgagat
 701 caaacgggcg gccgcaagcg cttggcgtca cccgcagttc ggtggttaat
 751 aagaattggc cgctcGAGCA TGCATCTAGA GCTCGCTGAT CAGCCTCGAC
 801 TGTGCCTTCT AGTTGCCAGC CATCTGTTGT TTGCCCCTCC CCCGTGCCTT
 851 CCTTGACCCT GGAAGGTGCC ACTCCCACTG TCCTTTCCTA ATAAAATGAG
 901 GAAATTGCAT CGCATTGTCT GAGTAGGTGT CATTCTATTC TGGGGGGTGG
 951 GGTGGGGCAG GACAGCAAGG GGGAGGATTG GAAGACAAT AGCAGGCATG
1001 CTGGGGATGC GGTGGGCTCT ATGGAACCAG CTGGGGCTCG AGGGGGGATC
1051 CCCACGCGCC CTGTAGCGGC GCATTAAGCG CGGCGGGTGT GGTGGTTACG
1101 CGCAGCGTGA CCGCTACACT TGCCAGCGCC CTAGCGCCCG CTCCTTTCGC
1151 TTTCTTCCCT TCCTTTCTCG CCACGTTCGC CGGCTTTCCC CGTCAAGCTC
1201 TAAATCGGGG CATCCCTTTA GGGTTCCGAT TTAGTGCTTT ACGGCACCTC
1251 GACCCCAAAA AACTTGATTA GGGTGATGGT TCACGTAGTG GGCCATCGCC
1301 CTGATAGACG GTTTTTCGCC CTTTGACGTT GGAGTCCACG TTCTTTAATA
1351 GTGGACTCTT GTTCCAAACT GGAACAACAC TCAACCCTAT CTCGGTCTAT
```

Fig. 4 (Part 1 of 3)

```
1401 TCTTTTGATT TATAAGGGAT TTTGGGGATT TCGGCCTATT GGTTAAAAAA
1451 TGAGCTGATT TAACAAAAAT TAACGCGAA TTTTAACAAA ATATTAACGT
1501 TTACAATTTA AATATTTGCT TATACAATCT TCCTGTTTTT GGGGCTTTTC
1551 TGATTATCAA CCGGGGTGGG TACCGAGCTC GAATTCTGTG AATGTGTGT
1601 CAGTTAGGGT GTGGAAAGTC CCCAGGCTCC CCAGGCAGGC AGAAGTATGC
1651 AAAGCATGCA TCTCAATTAG TCAGCAACCA GGTGTGGAAA GTCCCCAGGC
1701 TCCCCAGCAG GCAGAAGTAT GCAAAGCATG CATCTCAATT AGTCAGCAAC
1751 CATAGTCCCG CCCCTAACTC CGCCCATCCC GCCCCTAACT CCGCCCAGTT
1801 CCGCCCATTC TCCGCCCCAT GGCTGACTAA TTTTTTTTAT TTATGCAGAG
1851 GCCGAGGCCG CGAAATGACC GACCAAGCGA CGCCCAACCT GCCATCACGA
1901 GATTTCGATT CCACCGCCGC CTTCTATGAA AGGTTGGGCT TCGGAATCGT
1951 TTTCCGGGAC GCCGGCTGGA TGATCCTCCA GCGCGGGGAT CTCATGCTGG
2001 AGTTCTTCGC CCACCCCAAC TTGTTTATTG CAGCTTATAA TGGTTACAAA
2051 TAAAGCAATA GCATCACAAA TTTCACAAAT AAAGCATTTT TTTCACTGCA
2101 TTCTAGTTGT GGTTTGTCCA AACTCATCAA TGTATCTTAT CATGTCTGGA
2151 TCCCGTCGAC CTCGAGAGCT TGGCGTAATC ATGGTCATAG CTGTTTCCTG
2201 TGTGAAATTG TTATCCGCTC ACAATTCCAC ACAACATACG AGCCGGAAGC
2251 ATAAAGTGTA AAGCCTGGGG TGCCTAATGA GTGAGCTAAC TCACATTAAT
2301 TGCGTTGCGC TCACTGCCCG CTTTCCAGTC GGGAAACCTG TCGTGCCAGC
2351 TGCATTAATG AATCGGCCAA CGCGCGGGGA GAGGCGGTTT GCGTATTGGG
2401 CGCTCTTCCG CTTCCTCGCT CACTGACTCG CTGCGCTCGG TCGTTCGGCT
2451 GCGGCGAGCG GTATCAGCTC ACTCAAAGGC GGTAATACGG TTATCCACAG
2501 AATCAGGGGA TAACGCAGGA AGAACATGT GAGCAAAAGG CCAGCAAAAG
2551 GCCAGGAACC GTAAAAAGGC CGCGTTGCTG GCGTTTTTCC ATAGGCTCCG
2601 CCCCCCTGAC GAGCATCACA AAAATCGACG CTCAAGTCAG AGGTGGCGAA
2651 ACCCGACAGG ACTATAAAGA TACCAGGCGT TTCCCCCTGG AAGCTCCCTC
2701 GTGCGCTCTC CTGTTCCGAC CCTGCCGCTT ACCGGATACC TGTCCGCCTT
2751 TCTCCCTTCG GGAAGCGTGG CGCTTTCTCA ATGCTCACGC TGTAGGTATC
2801 TCAGTTCGGT GTAGGTCGTT CGCTCCAAGC TGGGCTGTGT GCACGAACCC
2851 CCCGTTCAGC CCGACCGCTG CGCCTTATCC GGTAACTATC GTCTTGAGTC
2901 CAACCCGGTA AGACACGACT TATCGCCACT GGCAGCAGCC ACTGGTAACA
2951 GGATTAGCAG AGCGAGGTAT GTAGGCGGTG CTACAGAGTT CTTGAAGTGG
3001 TGGCCTAACT ACGGCTACAC TAGAAGGACA GTATTTGGTA TCTGCGCTCT
```

```
3051 GCTGAAGCCA GTTACCTTCG GAAAAAGAGT TGGTAGCTCT TGATCCGGCA
3101 AACAAACCAC CGCTGGTAGC GGTGGTTTTT TTGTTTGCAA GCAGCAGATT
3151 ACGCGCAGAA AAAAAGGATC TCAAGAAGAT CCTTTGATCT TTTCTACGGG
3201 GTCTGACGCT CAGTGGAACG AAAACTCACG TTAAGGGATT TTGGTCATGA
3251 GATTATCAAA AAGGATCTTC ACCTAGATCC TTTTAAATTA AAAATGAAGT
3301 TTTAAATCAA TCTAAAGTAT ATATGAGTAA ACTTGGTCTG ACAGTTACCA
3351 ATGCTTAATC AGTGAGGCAC CTATCTCAGC GATCTGTCTA TTTCGTTCAT
3401 CCATAGTTGC CTGACTCCCC GTCGTGTAGA TAACTACGAT ACGGGAGGGC
3451 TTACCATCTG GCCCCAGTGC TGCAATGATA CCGCGAGACC CACGCTCACC
3501 GGCTCCAGAT TTATCAGCAA TAAACCAGCC AGCCGGAAGG GCCGAGCGCA
3551 GAAGTGGTCC TGCAACTTTA TCCGCCTCCA TCCAGTCTAT TAATTGTTGC
3601 CGGGAAGCTA GAGTAAGTAG TTCGCCAGTT AATAGTTTGC GCAACGTTGT
3651 TGCCATTGCT ACAGGCATCG TGGTGTCACG CTCGTCGTTT GGTATGGCTT
3701 CATTCAGCTC CGGTTCCCAA CGATCAAGGC GAGTTACATG ATCCCCCATG
3751 TTGTGCAAAA AAGCGGTTAG CTCCTTCGGT CCTCCGATCG TTGTCAGAAG
3801 TAAGTTGGCC GCAGTGTTAT CACTCATGGT TATGGCAGCA CTGCATAATT
3851 CTCTTACTGT CATGCCATCC GTAAGATGCT TTTCTGTGAC TGGTGAGTAC
3901 TCAACCAAGT CATTCTGAGA ATAGTGTATG CGGCGACCGA GTTGCTCTTG
3951 CCCGGCGTCA ATACGGGATA ATACCGCGCC ACATAGCAGA ACTTTAAAAG
4001 TGCTCATCAT TGGAAAACGT TCTTCGGGGC GAAAACTCTC AAGGATCTTA
4051 CCGCTGTTGA GATCCAGTTC GATGTAACCC ACTCGTGCAC CCAACTGATC
4101 TTCAGCATCT TTTACTTTCA CCAGCGTTTC TGGGTGAGCA AAAACAGGAA
4151 GGCAAAATGC CGCAAAAAAG GGAATAAGGG CGACACGGAA ATGTTGAATA
4201 CTCATACTCT TCCTTTTTCA ATATTATTGA AGCATTTATC AGGGTTATTG
4251 TCTCATGAGC GGATACATAT TTGAATGTAT TTAGAAAAAT AAACAAATAG
4301 GGGTTCCGCG CACATTTCCC CGAAAAGTGC CACCTGACGT C
```

Fig. 4 (Part 3 of 3)

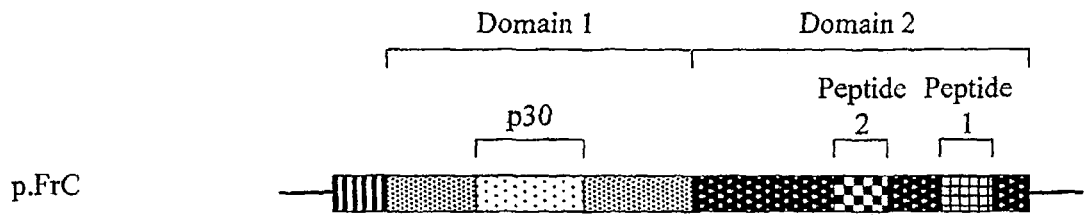
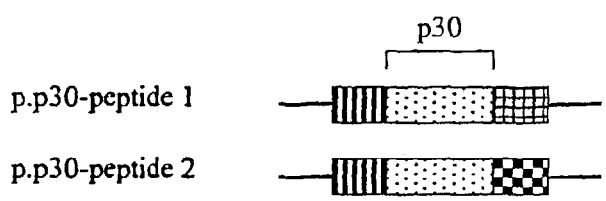
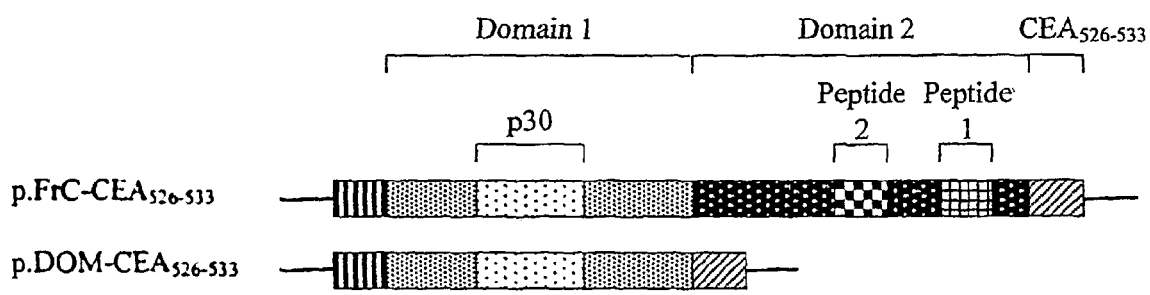
Fig. 7

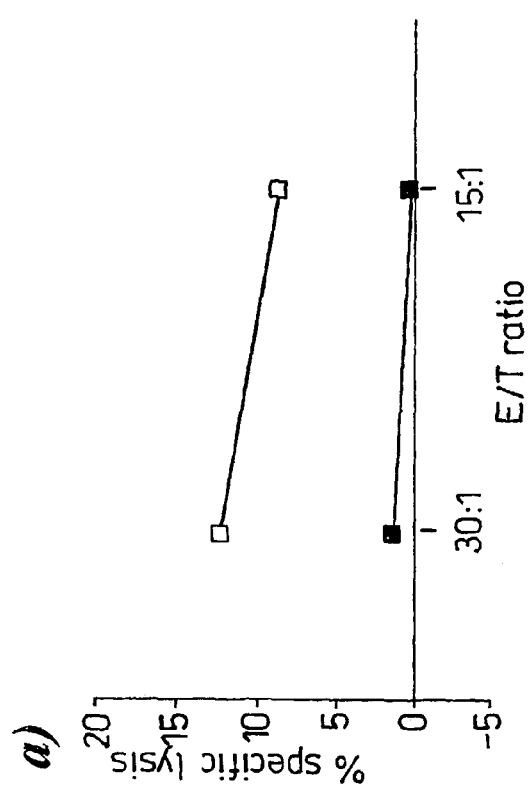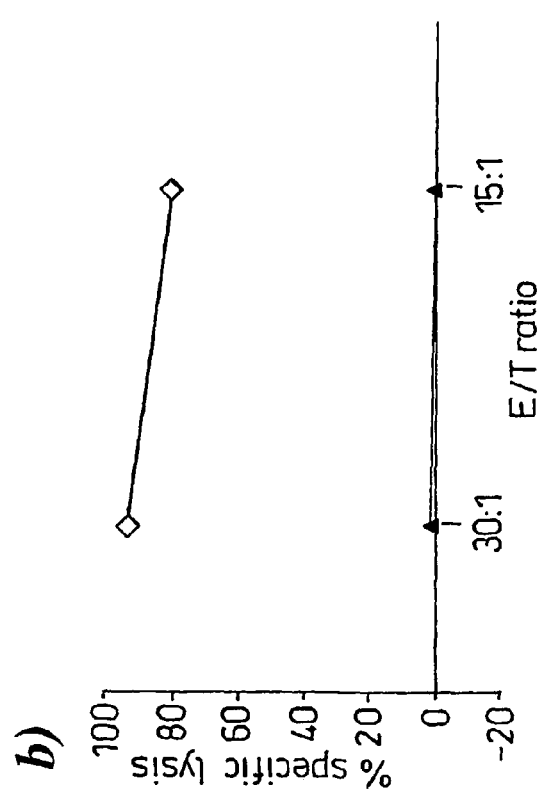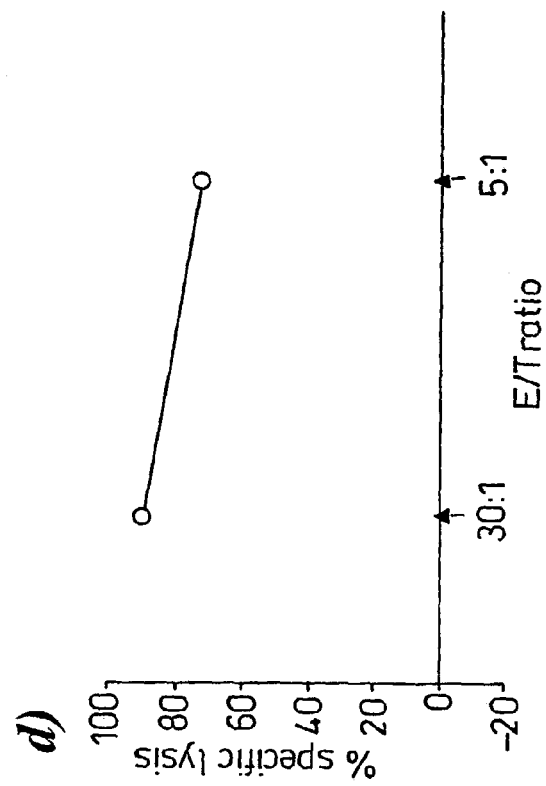
Fig. 11

SEQUENCE LISTING

<160> NUMBER OF SEQ ID NOS: 20

<210> SEQ ID NO 1
<211> LENGTH: 4341
<212> TYPE: DNA
<213> ORGANISM: Artificial Sequence
<220> FEATURE:
<223> OTHER INFORMATION: Description of Artificial Sequence: Vector pVAC1

<400> SEQUENCE: 1

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat taagctaca  acaaggcaag gcttgaccga caattgcatg aagaatctgc    180
ttagggttag gcgttttgcg ctgcttcgcg atgtacgggc cagatatacg cgtatctgag    240
gggactaggg tgtgtttagg cgaaaagcgg gcttcggtt gtacgcggtt aggagtcccc     300
tcaggatata gtagtttcgc ttttgcatag ggagggggaa atgtagtctt atgcaataca    360
cttgtagtct tgcaacatgg taacgatgag ttagcaacat gccttacaag gagagaaaaa    420
gcaccgtgca tgccgattgg tggaagtaag gtggtacgat cgtgccttat taggaaggca    480
acagacaggt ctgacatgga ttggacgaac cactgaattc gcattgcag  agataattgt    540 atttaagtgc ctagctcgat acaataaacg ccatttgacc attcaccaca ttggtgtgca    600
cctccaagct tagcatggac tggacctgga gggtcttctg cttgctggct gtggccccgg    660
gggcccactc ccaggtgcag ctgcaggtcg acctcgagat caaacgggcg ccgcaagcg     720 cttggcgtca cccgcagttc ggtggttaat aagaattggc cgctcgagca tgcatctaga    780
gctcgctgat cagcctcgac tgtgccttct agttgccagc catctgttgt ttgcccctcc    840
cccgtgcctt ccttgaccct ggaaggtgcc actcccactg tcctttccta ataaaatgag    900
gaaattgcat cgcattgtct gagtaggtgt cattctattc tggggggtgg ggtggggcag    960
gacagcaagg gggaggattg ggaagacaat agcaggcatg ctggggatgc ggtgggctct   1020
atggaaccag ctgggctcg  aggggggatc cccacgcgcc ctgtagcggc gcattaagcg   1080
cggcgggtgt ggtggttacg cgcagcgtga ccgctacact tgccagcgcc ctagcgcccg   1140
ctcctttcgc tttcttccct tcctttctcg ccacgttcgc cggctttccc cgtcaagctc   1200
taaatcgggg catccctta  gggttccgat ttagtgcttt acggcacctc gaccccaaaa   1260
aacttgatta gggtgatggt tcacgtagtg gccatcgcc  tgatagacg gttttcgcc    1320 ctttgacgtt ggagtccacg ttctttaata gtggactctt gttccaaact ggaacaacac   1380
tcaaccctat ctcggtctat tcttttgatt tataagggat tttggggatt cggcctatt    1440 ggttaaaaaa tgagctgatt taacaaaaat ttaacgcgaa ttttaacaaa atattaacgt   1500
ttacaattta aatatttgct tatacaatct tcctgttttt ggggcttttc tgattatcaa   1560
ccggggtggg taccgagctc gaattctgtg gaatgtgtgt cagttagggt gtggaaagtc   1620
cccaggctcc ccaggcaggc agaagtatgc aaagcatgca tctcaattag tcagcaacca   1680
```

-continued

```
ggtgtggaaa gtccccaggc tccccagcag gcagaagtat gcaaagcatg catctcaatt      1740
agtcagcaac catagtcccg cccctaactc cgcccatccc gccctaact ccgcccagtt       1800
ccgcccattc tccgcccat  ggctgactaa ttttttttat ttatgcagag gccgaggccg      1860
cgaaatgacc gaccaagcga cgcccaacct gccatcacga gatttcgatt ccaccgccgc      1920
cttctatgaa aggttgggct tcggaatcgt tttccgggac gccggctgga tgatcctcca      1980
gcgcggggat ctcatgctgg agttcttcgc ccaccccaac ttgtttattg cagcttataa      2040
tggttacaaa taaagcaata gcatcacaaa tttcacaaat aaagcatttt tttcactgca      2100
ttctagttgt ggtttgtcca aactcatcaa tgtatcttat catgtctgga tcccgtcgac      2160
ctcgagagct tggcgtaatc atggtcatag ctgtttcctg tgtgaaattg ttatccgctc      2220
acaattccac acaacatacg agccggaagc ataaagtgta aagcctgggg tgcctaatga      2280
gtgagctaac tcacattaat tgcgttgcgc tcactgcccg ctttccagtc gggaaacctg      2340
tcgtgccagc tgcattaatg aatcggccaa cgcgcgggga gaggcggttt gcgtattggg      2400
cgctcttccg cttcctcgct cactgactcg ctgcgctcgg tcgttcggct gcggcgagcg      2460
gtatcagctc actcaaaggc ggtaatacgg ttatccacag aatcagggga taacgcagga      2520
aagaacatgt gagcaaaagg ccagcaaaag gccaggaacc gtaaaaaggc cgcgttgctg      2580
gcgttttttcc ataggctccg cccccctgac gagcatcaca aaaatcgacg ctcaagtcag      2640
aggtggcgaa acccgacagg actataaaga taccaggcgt ttccccctgg aagctccctc      2700
gtgcgctctc ctgttccgac cctgccgctt accggatacc tgtccgcctt tctcccttcg      2760
ggaagcgtgg cgctttctca atgctcacgc tgtaggtatc tcagttcggt gtaggtcgtt      2820
cgctccaagc tgggctgtgt gcacgaaccc cccgttcagc ccgaccgctg cgccttatcc      2880
ggtaactatc gtcttgagtc caacccggta agacacgact tatcgccact ggcagcagcc      2940
actggtaaca ggattagcag agcgaggtat gtaggcggtg ctacagagtt cttgaagtgg      3000
tggcctaact acggctacac tagaaggaca gtatttggta tctgcgctct gctgaagcca      3060
gttaccttcg gaaaaagagt tggtagctct tgatccggca acaaaccac cgctggtagc       3120
ggtggttttt ttgtttgcaa gcagcagatt acgcgcagaa aaaaggatc tcaagaagat       3180
cctttgatct tttctacggg gtctgacgct cagtggaacg aaaactcacg ttaagggatt      3240
ttggtcatga gattatcaaa aaggatcttc acctagatcc ttttaaatta aaaatgaagt      3300
tttaaatcaa tctaaagtat atatgagtaa acttggtctg acagttacca atgcttaatc      3360
agtgaggcac ctatctcagc gatctgtcta tttcgttcat ccatagttgc ctgactcccc      3420
gtcgtgtaga taactacgat acgggagggc ttaccatctg gccccagtgc tgcaatgata      3480
ccgcgagacc cacgctcacc ggctccagat ttatcagcaa taaaccagcc agccggaagg      3540
gccgagcgca gaagtggtcc tgcaacttta tccgcctcca tccagtctat taattgttgc      3600
cgggaagcta gagtaagtag ttcgccagtt aatagtttgc gcaacgttgt tgccattgct      3660
acaggcatcg tggtgtcacg ctcgtcgttt ggtatggctt cattcagctc cggttcccaa      3720
cgatcaaggc gagttacatg atccccccatg ttgtgcaaaa aagcggttag ctccttcggt     3780
cctccgatcg ttgtcagaag taagttggcc gcagtgttat cactcatggt tatggcagca      3840
ctgcataatt ctcttactgt catgccatcc gtaagatgct tttctgtgac tggtgagtac      3900
tcaaccaagt cattctgaga atagtgtatg cggcgaccga gttgctcttg cccggcgtca      3960
atacgggata taccgcgcc acatagcaga actttaaaag tgctcatcat tggaaaacgt       4020
```

-continued

```
tcttcggggc gaaaactctc aaggatctta ccgctgttga gatccagttc gatgtaaccc   4080
actcgtgcac ccaactgatc ttcagcatct tttactttca ccagcgtttc tgggtgagca   4140
aaaacaggaa ggcaaaatgc cgcaaaaaag ggaataaggg cgacacggaa atgttgaata   4200
ctcatactct tcctttttca atattattga agcatttatc agggttattg tctcatgagc   4260
ggatacatat ttgaatgtat ttagaaaaat aaacaaatag gggttccgcg cacatttccc   4320
cgaaaagtgc cacctgacgt c                                              4341
```

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 2

```
Ser Asn Trp Tyr Phe Asn His Leu
 1               5
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 3

```
Leu Asn Ile Tyr Tyr Arg Arg Leu
 1               5
```

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 4

```
Glu Ala Gln Asn Thr Thr Tyr Leu
 1               5
```

<210> SEQ ID NO 5
<211> LENGTH: 8
<212> TYPE: PRT
<213> ORGANISM: Vesicular stomatitis virus

<400> SEQUENCE: 5

```
Arg Gly Tyr Val Tyr Gln Gly Leu
 1               5
```

<210> SEQ ID NO 6
<211> LENGTH: 8
<212> TYPE: PRT
<213> ORGANISM: Gallus domesticus

<400> SEQUENCE: 6

```
Ser Ile Ile Asn Phe Glu Lys Leu
 1               5
```

<210> SEQ ID NO 7
<211> LENGTH: 8
<212> TYPE: PRT
<213> ORGANISM: Sendai virus

-continued

<400> SEQUENCE: 7

Phe Ala Gly Asn Tyr Pro Ala Leu
  1               5

<210> SEQ ID NO 8
<211> LENGTH: 9
<212> TYPE: PRT
<213> ORGANISM: Influenza virus

<400> SEQUENCE: 8

Ala Ser Asn Glu Asn Met Asp Ala Met
  1               5

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 9
ttttaagctt gccgccacca tgggttggag c                                  31

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 10
aaaagcggcc gcttagttac cccagaagtc acgcag                             36

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 11
aaagcggccg cttacaggtg gttgaagtac cagttagagt taccccagaa gtcacgcag    59

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 12
aaagcggccg cttacagacg tcggtagtag atgttcaggt taccccagaa gtcacgcag    59

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 13
aaagcggccg cttacaggta ggttgtgttc tgagcctcgt taccccagaa gtcacgcag    59

<210> SEQ ID NO 14
<211> LENGTH: 61

-continued

```
<210> SEQ ID NO 14
<211> LENGTH: 61
<212> TYPE: DNA
<213> ORGANISM: Artificial Sequence
<220> FEATURE:
<223> OTHER INFORMATION: Description of Artificial Sequence: Primer

<400> SEQUENCE: 14
tttgcggccg cttacaggta ggttgtgttc tgagcctcgt cgttggtcaa ccttcatcgg    60
t                                                                   61

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
ctatataagc agagctct                                                  18

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 16
ggtgaagttg ttgaaggagt gcacacctgt agctgt                              36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 17
acaggtgtgc actccttcaa caacttcacc gttagc                              36

<210> SEQ ID NO 18
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 18
aaagcggccg cttacaggtg gttgaagtac cagttagatt ccaggtggga agcagaaac     59

<210> SEQ ID NO 19
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 19
aaagcggccg cttacagacg tcggtagtag atgttcagtt ccaggtggga agcagaaac     59

<210> SEQ ID NO 20
<211> LENGTH: 1315
<212> TYPE: PRT
<213> ORG

-continued

```
Met Pro Ile Thr Ile Asn Asn Phe Arg Tyr Ser Asp Pro Val Asn Asn
 1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
```

-continued

```
                420                 425                 430
Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845
```

-continued

```
Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
        995                 1000                1005

Gly Glu Val Arg Gln Ile Thr Phe Arg Asp Leu Pro Asp Lys Phe Asn
    1010                1015                1020

Ala Tyr Leu Ala Asn Lys Trp Val Phe Ile Thr Ile Thr Asn Asp Arg
1025                1030                1035                1040

Leu Ser Ser Ala Asn Leu Tyr Ile Asn Gly Val Leu Met Gly Ser Ala
                1045                1050                1055

Glu Ile Thr Gly Leu Gly Ala Ile Arg Glu Asp Asn Asn Ile Thr Leu
            1060                1065                1070

Lys Leu Asp Arg Cys Asn Asn Asn Asn Gln Tyr Val Ser Ile Asp Lys
        1075                1080                1085

Phe Arg Ile Phe Cys Lys Ala Leu Asn Pro Lys Glu Ile Glu Lys Leu
    1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
                1125                1130                1135

Ser Lys Asp Val Gln Leu Lys Asn Ile Thr Asp Tyr Met Tyr Leu Thr
            1140                1145                1150

Asn Ala Pro Ser Tyr Thr Asn Gly Lys Leu Asn Ile Tyr Tyr Arg Arg
        1155                1160                1165

Leu Tyr Asn Gly Leu Lys Phe Ile Ile Lys Arg Tyr Thr Pro Asn Asn
    1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
                1205                1210                1215

Ala Phe Asn Asn Leu Asp Arg Ile Leu Arg Val Gly Tyr Asn Ala Pro
            1220                1225                1230

Gly Ile Pro Leu Tyr Lys Lys Met Glu Ala Val Lys Leu Arg Asp Leu
        1235                1240                1245

Lys Thr Tyr Ser Val Gln Leu Lys Leu Tyr Asp Asp Lys Asn Ala Ser
    1250                1255                1260
```

```
                                          -continued
Leu Gly Leu Val Gly Thr His Asn Gly Gln Ile Gly Asn Asp Pro Asn
1265                1270            1275                1280

Arg Asp Ile Leu Ile Ala Ser Asn Trp Tyr Phe Asn His Leu Lys Asp
                1285            1290                1295

Lys Ile Leu Gly Cys Asp Trp Tyr Phe Val Pro Thr Asp Glu Gly Trp
                1300            1305            1310

Thr Asn Asp
       1315
```

MATERIALS AND METHODS RELATING TO IMMUNE RESPONSES TO FUSION PROTEINS

This application is a §371 application of PCT/GB01/01719, filed on 17 Apr. 2001, which in turn claims priority to GB application 0009470.6 filed 17 Apr. 2000. Each of the above identified applications is incorporated by reference herein.

FIELD OF THE INVENTION

The present invention relates to materials and methods involved in inducing an immune response in an individual. Particularly, but not exclusively, the present invention relates to DNA vaccines comprising Fragment C (FrC) domains as adjuvants for raising cytotoxic T lymphocytes (CTLs) against disease peptide antigens.

BACKGROUND OF THE INVENTION

While acellular vaccines are inevitably safer than vaccines based on whole organisms, a fully effective vaccine cannot normally be made from a single isolated constituent of a microorganism, and it is now clear that this is because of the need to activate more than one cell type to initiate an immune response. One consequence of this insight has been the development of conjugate vaccines.

However, even conjugate vaccines are not usually strongly immunogenic on their own. Most of them require the addition of adjuvants: substances that enhance immunogenicity of antigens. It is thought that most, if not all, adjuvants act on antigen-presenting cells (APCs) and reflect the importance of these cells in initiating immune responses. *H. influenzae* polysaccharides, for example, have been conjugated to tetanus toxoid because infants are vaccinated routinely with this protein and their T cells are already primed against it.

Tetanus toxin has been studied in detail. For example, see Umland T. C. et al, Nature Structural Biology, Vol. 4 No. 10 1997. A transport mechanism is exploited by the toxin for delivery to its cytotoxic target within the central nervous system. The receptor binding subunit of tetanus toxin plays a dominant role in this delivery process. This receptor binding subunit is known as $H_C$ and is composed of the 50,000 Mr fragment from the C-terminal end of the heavy chain of tetanus toxin. Historically, 50,000 Mr fragment has been termed the Fragment C (FrC). Isolated FrC retains the capability of being transported to the CNS in a manner similar to that of the intact tetanus toxin.

Tetanus toxoid has been used as a carrier protein for inducing immune responses against peptides (Herrington et al, 1992 J. Immunol. 149:717). There is considerable information available on immune responses against tetanus toxoid and the epitopes recognized by human CD4+ T cells (Valmori et al, 1992 J. Immunol. 149:717), as well as the mechanisms involved in enhancing immunity to added peptides (Panina-Bordignon et al, 1989 Eur. J. Immunol. 19:2237; Kumar 1992 J. Immunol, 148:1499). Fragment C (FrC), the 50 kD carboxy-terminal portion of the heavy chain of tetanus toxin, has been found to induce protective immunity again tetanus toxin which is largely antibody-mediated (Anderson et al, 1996. Infect. and Immun. 64:3168).

Previous work (King, C. A. et al, Nature Medicine, 1998, Vol. 4 p. 1281), jointly authored by a co-inventor of the present invention, describes the use and production of nucleic acid constructs for inducing an immune response in a mammal to a disease antigen present on a malignant B cell in the mammal. The DNA construct directs the expression of a fusion protein which comprises the tumour antigen and the tetanus toxin Fragment C (FrC). Thus, it has already been shown that an immune response to a given antigen can be enhanced by the presence of FrC itself.

SUMMARY OF THE INVENTION

The T-cell helper sequence p30 of Fragment C, from tetanus toxin, has the ability to activate CD4$^+$ T-cells and has been used in constructs to help initiate an immune response to an antigen. However, it has been found that at the DNA level, for example, DNA vaccines, the isolated helper sequence is not as effective as hoped. This may be because the isolated helper sequence is not sufficient in order to prime or even to be recognised by the immune system. Thus, the present inventors have appreciated that an effective DNA vaccine must not only comprise the helper sequence but also sequence capable of priming the immune system. As mentioned above, effective DNA vaccines comprising tumour antigens linked to the complete Fragment C have been provided. However, the present inventors have now surprisingly found that the induction of an immune response to a disease peptide antigen can be improved and simplified by using a certain component of the Fragment C rather than the entire fragment.

The inventors have assembled a nucleic acid sequence encoding the first domain of FrC, which contains helper sequence(s) (e.g. p30), and linked it to a peptide-encoding sequence which has the ability to induce cytotoxic T-cell (CTL) responses. When the inventors injected the vector into mice, they saw a very rapid induction of CTLs. This induction was considerably faster than if the peptide had to be processed from its natural surrounding sequence. Indeed, the inventors have compared (i) a DNA vaccine containing full length FrC (2 domains) linked to an endogenous tumour antigen, with (ii) the one domain FrC format linked to a specific CTL epitope taken from the tumour antigen. The latter vaccine (ii) induced higher levels of CTLs. These levels remained higher even at day 55 post vaccination, as compared to the 2-domain vaccine.

Thus, the present inventors have for the first time determined a design of vaccine which contains all the ingredients for inducing immunity, i.e. helper sequence, and an activating sequence within the first domain of FrC which starts the priming process. The second domain of Fragment C comprises a number of cytotoxic T-cell motifs and it is believed by the inventors that these motifs may well compete with the motifs present in the disease antigen present in the fusion protein. With these motifs absent, the DNA vaccine has improved efficiency at inducing immunity.

Put broadly, therefore, the invention resides in the idea to use nucleic acid which encodes the first domain of FrC, but which lacks nucleic acid sequence(s) encoding one or more T cell epitopes of the second domain of FrC in a nucleic acid construct encoding a fusion polypeptide also comprising a disease antigen. The lack of the second domain improves the ability of the fusion polypeptide to induce a T-cell response against the disease antigen. The nucleic acid need not necessarily lack sequence encoding the entire second domain, however. For example, it is contemplated that some portion of the second domain might be present without adversely affecting the ability of the fusion polypeptide to induce a T-cell response. Preferably at least nucleic acid encoding peptide 1 and/or peptide 2 as identified herein is absent. More preferably, since other T cell epitopes may be present in the naturally occurring second domain, no more than an insubstantial part of the second domain is encoded by the nucleic acid. An insubstantial part may comprise less than 50%, less than 40%, less than 30%, 25%, 20%, 15%, 10% or less than 5% of the amino acids of the naturally occurring second domain of Fragment C.

While the following refers frequently to idiotypic antigens, the invention is not limited to such antigens, but may utilise any suitable disease antigens, particularly tumour antigens (such as a fragment of CEA), often small antigens for T cell induction.

More specifically, therefore, in a first aspect of the present invention, there is provided a nucleic acid construct for delivery into living cells in vivo for inducing an immune response in a patient to a disease peptide antigen; the construct directing the expression of a fusion protein, said fusion protein comprising the disease peptide/polypeptide antigen and the first domain of FrC.

The first domain of the FrC fragment comprises helper sequence(s) (particularly p30). The FrC domain acts as an adjuvant, which helps, boosts or primes the immune system and enabling it to respond to the disease antigen by inducing CTLs. As used herein, the term "first domain" preferably refers to an entire naturally occurring first domain of FrC. However, it is contemplated that minor sequence variations may be introduced without significantly affecting the ability of the fusion protein to induce T cell responses, and fusion proteins having a first domain of FrC including such variations are also included within the scope of the invention. Preferably the first domain of FrC encoded by the nucleic acid of the invention has at least 50%, more preferably at least about 60%, 70%, 80%, 90%, 95%, 98% or 99% amino sequence identity with a naturally occurring first domain of FrC (with identity determined by the NCBI-BLAST2 algorithm of Altschul et al. *Nucleic Acid Res.* 25:3389-3402 (1997) using default parameters). More preferably it contains an amino acid sequence having at least 75%, 80%, 85%, 90%, 95%, 98%, or 99% amino acid sequence identity with the p30 helper sequence.

The inventors initially supposed that the one domain FrC vaccine format is capable of inducing higher numbers of CTLs, as compared to the two domain format when the DNA encoding the antigen of choice is fused to the 3'-terminus (carboxy end of the resulting protein) of the single domain of the FrC. However, following several experiments, the inventors have now determined that the impressive CTL response is also observed if the antigen/epitope is linked to the other end of the vaccine, at the start of the FrC domain (5'-terminus of the DNA, or the amino terminus of the resulting protein). This therefore raises the possibility of using either end or both ends of the FrC domain to associate to the antigen/epitope.

As described in Umland T. C. et al, Nature Structural Biology, Vol. 4 No. 10 1997, FrC has two main domains. The two domains are separated naturally in FrC by a linking amino acid sequence. The inventors have found that if this linking amino acid sequence is cut at the DNA level, a DNA sequence encoding a peptide of choice (e.g. a tumour or pathogen antigen) can be added to either the C-terminus or the N-terminus of the first domain which comprises helper sequence(s) (e.g. p30) and priming sequence. The two domains are identified in Umland et al and are shown again in FIG. 1. The p30 helper sequence may be found at amino acid positions 947 to 967.

The disease peptide antigen may be any peptide sequence that comprises one or more epitopes characteristic of that disease. For example, the peptide may comprise epitopes characteristic of a particular infectious disease, pathogen or cancer (tumour antigen). The term "peptide" is not intended to imply any particular size restriction, and may embrace large polypeptides and proteins of up to at least several hundred amino acids, such as MUC-1 and gp70. Preferably, however, the peptide has between 5 and 40 amino acids, more preferably between 5 and 30, still more preferably between 7 and 25 amino acids (desirably between 7 and 10 amino acids), further preferably between 8 and 25 amino acids. Many cancer peptides are known and published. Candidates from melanoma such as MAGE and tyrosinase antigens or mutated proto-oncogenes such as Ras. These sequences are all published so it would be well within the capabilities of the skilled person to obtain them and place them in the FrC domain-containing vector according to the present invention. A useful review describing some of the candidate tumour sequences which could be targeted by CTLs is Henderson R. A. and Finn O. J. (1996) "Human tumor antigens are ready to fly" Adv. in Immunology 62:217.

The peptide may also be an idiotypic determinant which is preferably present in the fusion protein in essentially the same conformation as that which it adopts on the surface of malignant B cells, thereby optimising the efficiency of the anti-idiotypic immune response induced by the fusion protein. With regard to idiotypic determinants, optimising the efficiency of the immune response may be achieved by expression of the idiotypic determinant within the context of a portion of an immunoglobulin (Ig) molecule or immunoglobulin-like molecule, such as a single chain Fv (scFv) fragment. The scFv fragment is particularly convenient, providing the necessary structural features of the idiotypic determinant with few extraneous amino acid residues. However, if desired additional amino acid residues could be included in the fusion protein, such as one or more constant domains (e.g. Syrengelas et al, 1996 Nature Medicine 2, 1038). Thus, for example, one could express the idiotypic determinant in the context of an entire immunoglobulin molecule.

In a preferred embodiment, the fusion protein is expressed with a leader sequence (recognised in human cells) which directs the fusion protein to the endoplasmic reticulum, where the leader sequence is cleaved from the fusion protein. In this way, the fusion protein will be correctly folded before leaving the cell. The correct folding of the fusion protein is important as this will ensure that the epitopes characteristic of the disease in question are displayed appropriately to the immune system. A large number of suitable leader sequences are known including, for example, the leader sequences (such as that for $V_H1$ described below) found at the 5' end of human V genes. Such leader sequences have been found by the present inventors to increase the immunogenicity of the fusion protein. In principle, any other leader sequence is likely to exert an equivalent advantageous effect, but it is probable that those most similar to the natural immunoglobulin-type leader sequence will be optimal.

For the sake of convenience, the nucleic acid construct will preferably comprise a number of restriction endonuclease recognition sites. In particular, if the construct is designed with the FrC domain linked upstream of the disease CTL epitope sequence, one or more such recognition sites may be located 5' of the sequence encoding the FrC first domain (possibly between the optional leader sequence and the sequence encoding the FrC domain), and one or more sites may be located 3' of the sequence encoding the disease antigen. In this way, the same basic construct can readily be adapted to express different fusion proteins in which the disease antigen may be altered. Thus, sequences encoding disease antigens such as idiotypic determinants from different patients can easily be introduced into the construct.

Figure 3:
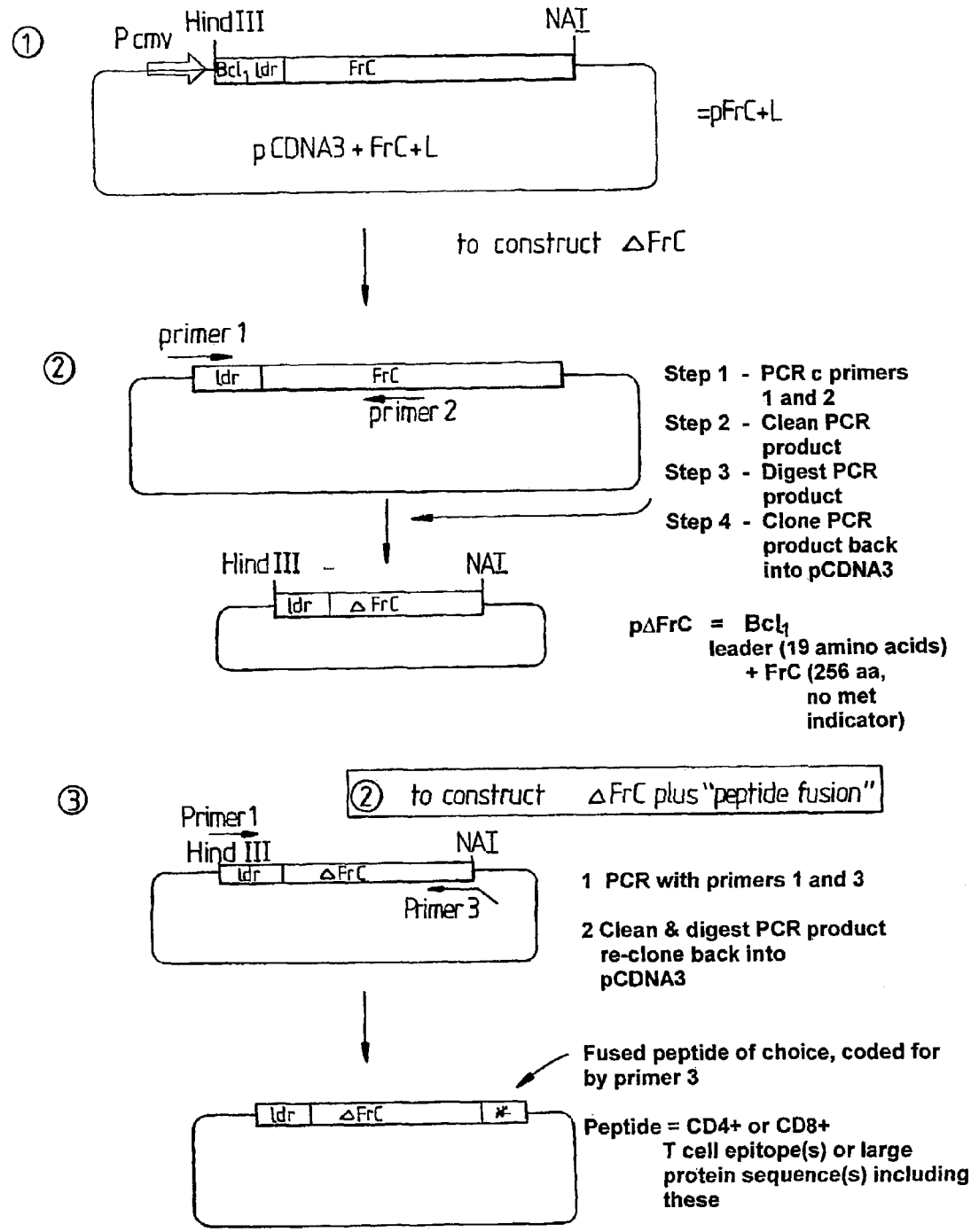
Figure 5:
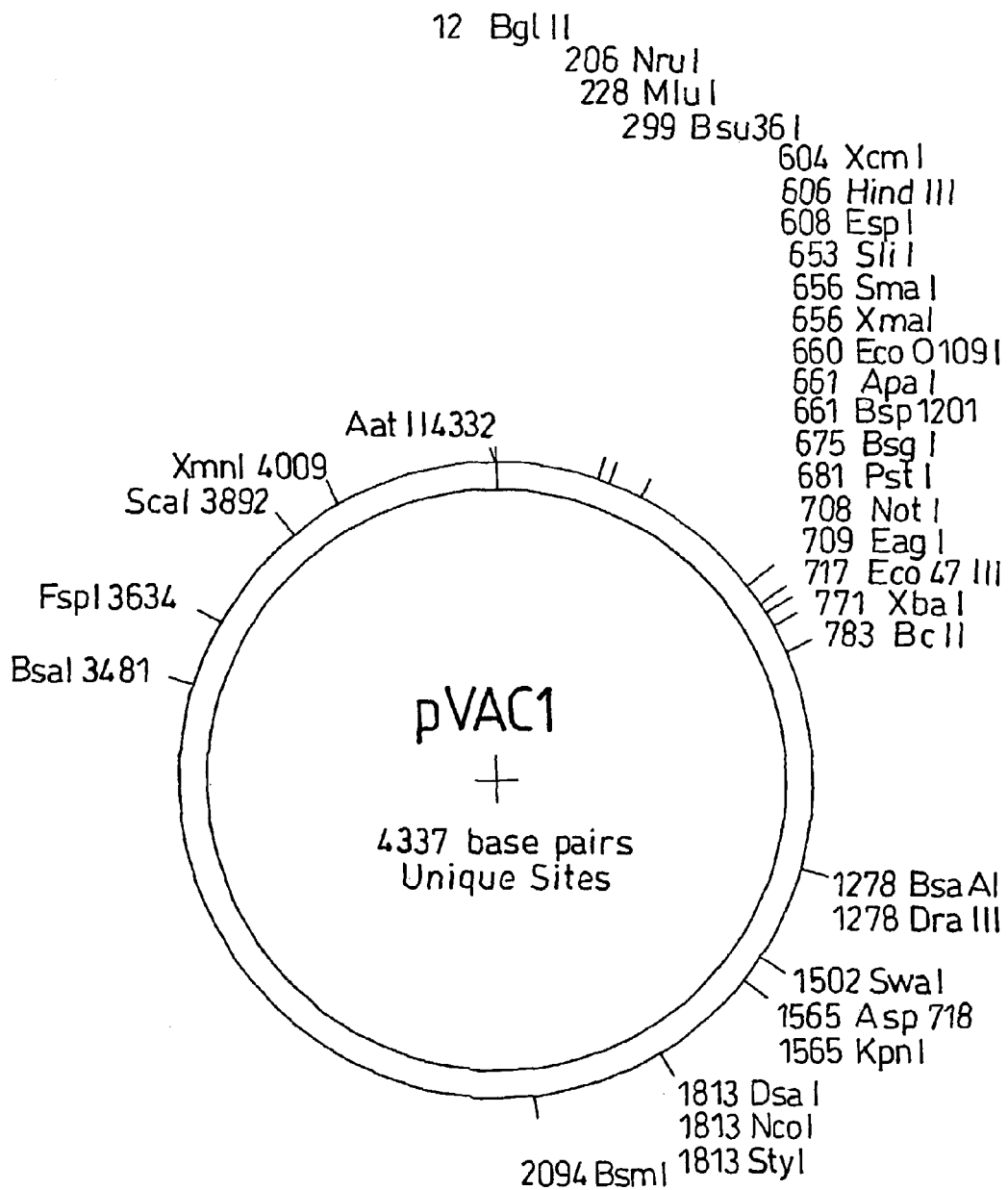

An alternative method for associating a disease antigen (especially a small antigen) with the FrC domain is shown in FIG. 3, part 3, and described below.

In a particular embodiment this invention provides a vaccine nucleic acid which can be used to elicit an immune response against transformed human lymphocytes displaying an idiotypic marker, the nucleic acid encoding proteins comprising the heavy and light chain variable regions of an anti-idiotypic antibody displayed on surface of a malignant human B-cell or T-cell.

In a second aspect, the invention provides a method of making a nucleic acid construct for inducing an immune response in a patient, the method comprising:
(a) identifying a nucleic acid sequence encoding a disease peptide antigen comprising epitopes characteristic of said disease;
(b) cloning the nucleic acid sequence encoding the disease peptide antigen; and
(c) introducing the cloned nucleic acid into a vector, which vector allows for the disease peptide antigen to be expressed as a fusion protein with the first domain of FrC from tetanus toxin.

The vector comprising the first domain of FrC may also conveniently comprise a leader sequence for association with the fusion protein, e.g. 5' of the FrC domain. The vector may be prepared as part of the method, or it may be produced in advance ready to incorporate the desired disease peptide antigen. In this way, nucleic acid primers may be designed which are capable of introducing the nucleic acid encoding the disease antigen into the vector during a PCR technique. This is described in the detailed description. A vector comprising the first domain of FrC and a leader sequence forms a further aspect of the present invention, and it may be provided as part of a kit. Preferably the vector comprises restriction sites so that the nucleic acid encoding the disease antigen can be inserted into the vector with ease. In an alternative example, a nucleic acid encoding the leader sequence, FrC domain and disease antigen can be prepared (e.g. by PCR) and inserted as a single fusion (using suitable restriction sites) into a vector comprising suitable regulatory regions.

As mentioned above, the disease antigen any be any peptide comprising epitopes characteristic of a particular disease, e.g. tumour antigens, pathogens and idiotypic determinants. For convenience, the following text describes the case where the disease antigen is an idiotypic determinant. However, the skilled person would have no difficulty in adapting this teaching to the use of other disease antigens and the present invention is not limited to the use of idiotypic determinants.

Therefore, by way of example, nucleic acid encoding the idiotypic determinant may be cloned from a sample comprising the patient's cells by PCR. A large family of suitable generic PCR primers, capable of recovering nucleic acid sequences encoding essentially any B cell idiotypic determinant, is now available (Hawkins & Winter, 1992 Eur. J. Immunol. 22, 876). Typically the B cell malignancy is a lymphoma. Generally, the nucleic acid construct made by the method defined above will be in accordance with the first aspect of the invention.

The first and second domains are separated naturally in FrC by a linking amino acid sequence. This linking amino acid sequence may be cut at the DNA level so that the nucleic acid sequence encoding the peptide comprising the disease antigen may be linked to the C-terminus of the first domain and the second domain discarded. The disease antigen is added at the DNA level and is effectively linked to either the C-terminus or the N-terminus of the FrC first domain. The thus formed nucleic acid construct is then placed in a DNA vector.

The vector backbone is preferably a bacterial DNA comprising the appropriate control sequences to direct gene expression. Standard PCR and ligation steps known to the skilled person may then be used to introduce the DNA construct into the vector. The DNA vector may then be injected into the patient, via, for example, muscle cells. The DNA enters the muscle cell where the nucleic acid construct encoding the fusion protein comprising the first domain of FrC and the disease antigen is read. Following transcription and translation the fusion protein is expressed. As the protein is perceived as foreign to its surroundings, it is then presented to the immune system. Activation of immunity is assisted by the presence of "immunostimulatory sequences" in the bacterial DNA backbone of the vector. Thus, the outcome is the presentation of the encoded protein to the immune cells of the host.

In a third aspect, the invention provides a method for treating a patient suffering from a disease, the method comprising administering to the patient a nucleic acid construct in accordance with the first aspect of the invention defined above, so as to induce an immune response to the disease. Further, the present invention provides use of the nucleic acid construct in accordance with the first aspect of the present invention in the preparation of a medicament for treatment of a disease, such as an infectious disease or a cancer.

In the case of idiotypic determinants, preferably the nucleic acid sequence encoding the idiotypic determinant is cloned from samples obtained from the individual to whom it is delivered. Conveniently the nucleic acid sequence is delivered in unencapsidated form (i.e. not enclosed within a viral particle or other package). The nucleic acid may, however, be associated with the external surface of a package or particle (e.g. a liposome or a viral particle), which allows for the possibility of receptor-mediated delivery of the nucleic acid.

The fusion protein may direct the expression of the disease antigen and the FrC first domain alone. Alternatively the fusion protein may additionally comprise further immunomodulatory polypeptide sequences, such as other foreign immunogenic proteins, or cytokines. Indeed it may be valuable to use several antigenic fusion partners to help prevent the theoretical problem that the immune response to the highly immunogenic moiety of the fusion protein could ultimately overwhelm any response to the relatively weakly immunogenic disease antigen (although the single-domain FrC-antigen fusion format has been designed to reduce this). Coat proteins of enveloped viruses and immunogenic cell surface or secreted proteins derived from any pathogenic organism or non-human species may be suitable for inclusion in the fusion protein. An alternative modification is to design the nucleic acid construct so as to allow for the co-expression of the further immunomodulatory polypeptides as separate entities rather than as fusions with the disease antigen/FrC first domain. Less preferably, the method of the invention could employ the use of a separate nucleic acid construct to express the further immunomodulatory polypeptides.

A number of cytokines are known to improve aspects of antigen presentation and the direct delivery of expression vectors containing cytokine genes could enhance vaccine efficacy. Interferon gamma is one example which could be useful due to the property of upregulating MHC expression (Gaczynska et al. 1993 Nature 365, 264-267). Another polypeptide which could be expressed by the vaccine nucleic acid is granulocytelmacrophage-colony stimulating factor (GM-CSF). The relevant gene could be encoded on the same, or on a separate, vector and the amount of polypeptide expressed varied independently.

One advantage of the genetic approach to vaccination is that it potentially allows efficient use of the natural method of presenting antigen, which should therefore engage a wide range of effector systems. Moreover, manipulation and improvement of the response obtained should be relatively easy; for example, it may be possible to improve the efficiency of presentation of antigen to T cells by expressing molecules with co-stimulatory activity together with the immunogen. One important molecule involved in co-stimulation is B7, which interacts with CD28 expressed by T cells thereby providing accessory signals for T-cell activation (Galvin et al., 1992 J. Immunol. 12, 3802-3808). Vectors could be constructed which express both B7 and the single-domain Fragment C fusion. Sequences of both mouse and human B7 are published (Freeman et al., 1989 J. Immunol. 8, 2714-2722) and the genes may readily be cloned by PCR.

It is thus an optional feature of the present invention that the method further comprises the delivery of a second nucleic acid sequence to the individual which directs the expression of a further immunomodulatory polypeptide for the purpose of further modulating the immune response to the disease antigen. This second nucleic acid sequence may be comprised on the same nucleic acid molecule as the first nucleic acid sequence, or may be present on a second nucleic acid molecule.

Methods of introducing the nucleic acid construct into living cells in vivo are now well known to those skilled in the art. Conveniently the nucleic acid is simply injected as naked DNA into the patient (typically intramuscularly) as a mixture with a physiologically acceptable diluent, such as saline solution. Details of some suitable methods and preferred embodiments of the administration of the nucleic acid construct into a patient are described in U.S. Pat. Nos. 5,580,859 and 5,589,466. More involved methods of gene transfer include the use of viral vectors, encapsulating the DNA into liposomes, coupling of DNA to cationic liposomes or to the outside of viruses (for review see Miller, 1992 Nature 357, 45-46). These have the advantage of increased efficiency of transfer but, by comparison with direct injection of purified plasmid DNA, these alternative approaches are somewhat involved and raise more safety issues.

In a fourth aspect the invention therefore provides a composition for use in a method of inducing an immune response in a patient suffering from a disease (according to the third aspect of the invention defined above), the composition comprising a nucleic acid construct directing the expression of a fusion protein, said fusion protein comprising a disease antigen comprising epitopes characteristic of said disease and a helper sequence (preferably the p30 helper sequence) of FrC from tetanus toxin, together with a physiologically acceptable diluent or carrier. Preferably, the helper sequence of the FrC domain is comprised within the first domain of FrC such that the fusion protein comprises the first domain of FrC linked to the disease antigen in question. Indeed, it has been found that the first domain of FrC (which includes the p30 helper sequence) when fused to a disease antigen is much more effective at producing a T cell response (especially cytotoxic T cells) than the p30 helper sequence alone.

Ideally a vaccine should be capable of stimulating antigen-specific B cells, cytotoxic T lymphocytes (CTLs) and helper T cells. B cell stimulation requires that the target antigen should bind with sufficiently high affinity to specific antigen receptors (surface Ig) on the B-cell surface. Certain multivalent antigens can stimulate B cell proliferation directly but more often, and to provide an effective anamnestic response, there is a requirement for additional signals provided by helper T cells (see below). In the present invention, T cell help is recruited by expressing the disease antigen as a fusion protein with the helper sequence, preferably comprised within the first domain, of FrC from tetanus toxin.

The T cell receptors (TCRs) of CTLs recognise specific MHC class I-associated peptides displayed at the target cell surface. Such peptides are generally derived by processing of larger polypeptides or proteins manufactured within the target cell. Thus, for efficient CTL stimulation the target antigen should be synthesised or processed intracellularly in MHC class 1-expressing cells able to activate CTLs. The level of expression should be high enough to generate sufficient peptide to displace those self peptides which are normally bound (possibly with higher affinity) in the MHC peptide-binding groove (Ohno, 1992 PNAS 89, 4643-4647). Similar to antigen-specific B cells, for proliferation and increased cytotoxic capability, CTLs require additional signals (in the form of cytokines) following antigen recognition and these are provided by helper T cells.

CD4-positive helper T cells interact (via their unique TCRs) with specific cell surface MHC class II-associated peptides and such peptides are generally derived by proteolytic cleavage of protein antigens internalised by specialised antigen presenting cells (APCs). Macrophages, dendritic cells and B lymphocytes are amongst the cells which can present antigen in this way. Thus, B lymphocytes internalise and process antigen bound to their surface Ig and subsequently present MHC class II-associated derivative peptides (they can also present in class I). CD4-positive T helper cells recognising the surface peptide can then release various immunostimulatory cytokines and stimulate further B cell activation, proliferation and antibody production. Similarly, macrophages present at the site of a local inflammatory response can process phagocytosed antigen and stimulate cytokine release by T helper cells, leading to enhanced activation, proliferation and cytotoxicity of locally resident CTLs.

The vaccine antigen should therefore ideally 1) be synthesised intracellularly by MHC class I-positive host cells, 2) give rise to peptides which, when displayed by host cell class I MHC can stimulate a subset of host CTLs via their TCRs, 3) give rise to peptides which, when displayed by host cell class II MHC can stimulate a subset of host helper T cells via their TCRs, 4) be internalised and processed by host APCs including both macrophages and antigen-specific B cells, 5) be available in its native form for interaction with host B lymphocytes.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 1 shows the topology of FrC (Umland T. C. et al, Nature Structural Biology, Vol. 4 No. 10 1997). This figure shows the N-terminal or first domain and the C-terminal or second domain of FrC (SEQ ID NO: 1). The helper amino acid sequence is found at amino acid positions 947 to 967 in the first domain.

FIG. 2 shows a detailed map of a plasmid pcDNA3 (Invitrogen).

FIG. 3 shows a schematic representation of the method to produce a vector comprising first domain of FrC and the disease antigen.

FIG. 4 shows the entire sequence of the vector pVAC1.

FIG. 5 shows a pVAC1 restriction map.

Figure 6:
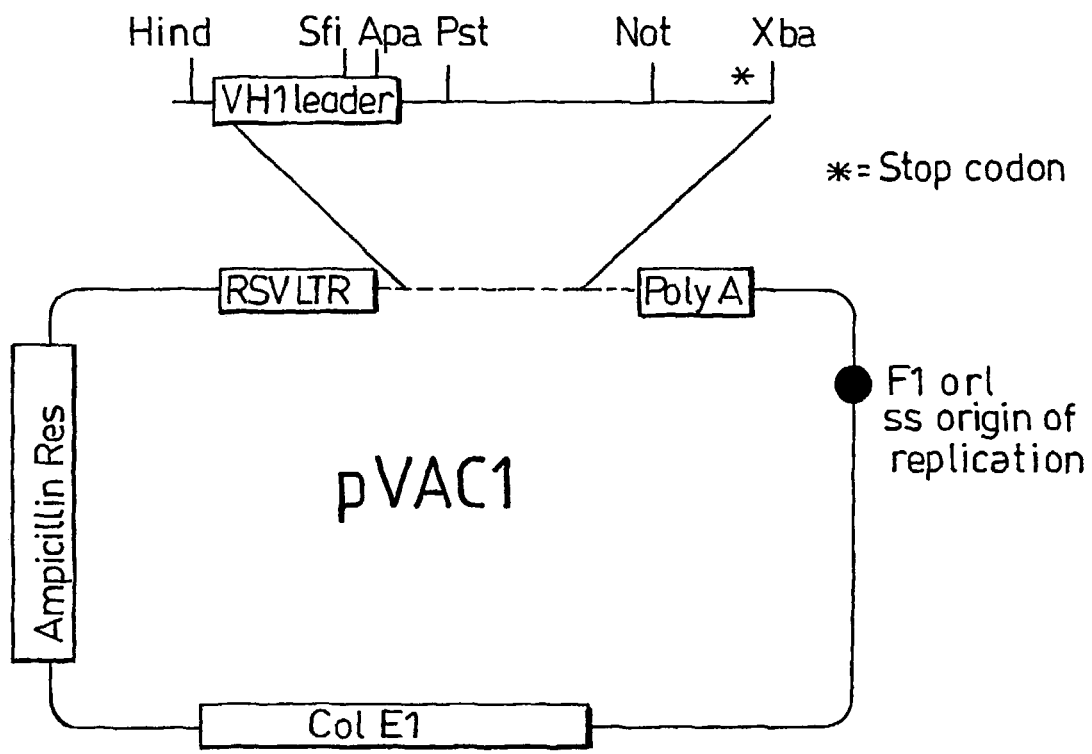

FIG. 6 shows a schematic representation of the main features of pVAC1.

FIG. 7 shows a schematic diagram indicating DNA vaccine design. Vaccine sequences were assembled and inserted into pcDNA3 using Hind III and Not I restriction enzyme sites. DNA sequences included those encoding the two domains of full length FrC (▆ and ▇), or the amino terminal domain only (▤), p30 (▣), BCL$_1$ leader (▥), TT$_{1287-1294}$ (peptide 1,▦), TT$_{1162-1169}$ (peptide 2,▧) and CEA$_{526-533}$ (▨). The DNA sequence encoding the T-helper epitope, p30, is in the p.DOM sequence (▆), the H-2K$^b$-restricted CTL epitopes TT$_{1287-1294}$ (peptide 1) and TT$_{1162-1169}$ (peptide 2) are in the second (▇) domain.

FIG. 8 shows CTL responses induced by vaccination with DNA encoding full length FrC sequence (p.FrC) are specific for two H2-K$^b$-binding octamers. Following vaccination with p.FrC, splenocytes taken at day 14 were restimulated with each of 8 peptides with significant predicted H-2K$^b$-binding activity. Only two peptides induced measurable CTL activity as measured by $^{51}$Cr release assay. a). CTL activity against peptide-loaded EL4 cells was detected against peptide 1 (SN-WYFNHL) and peptide 2 (LNIYYRRL). Each peptide was used reciprocally as either test or control. b). Binding activity to H-2K$^b$ by a stabilization assay showed that peptides 1 and 2 were comparable to the positive control from Sendai virus nucleoprotein (SEV), and clearly distinct from the control H-2D$^b$-binding peptide from influenza virus (ASN).

Figure 9:
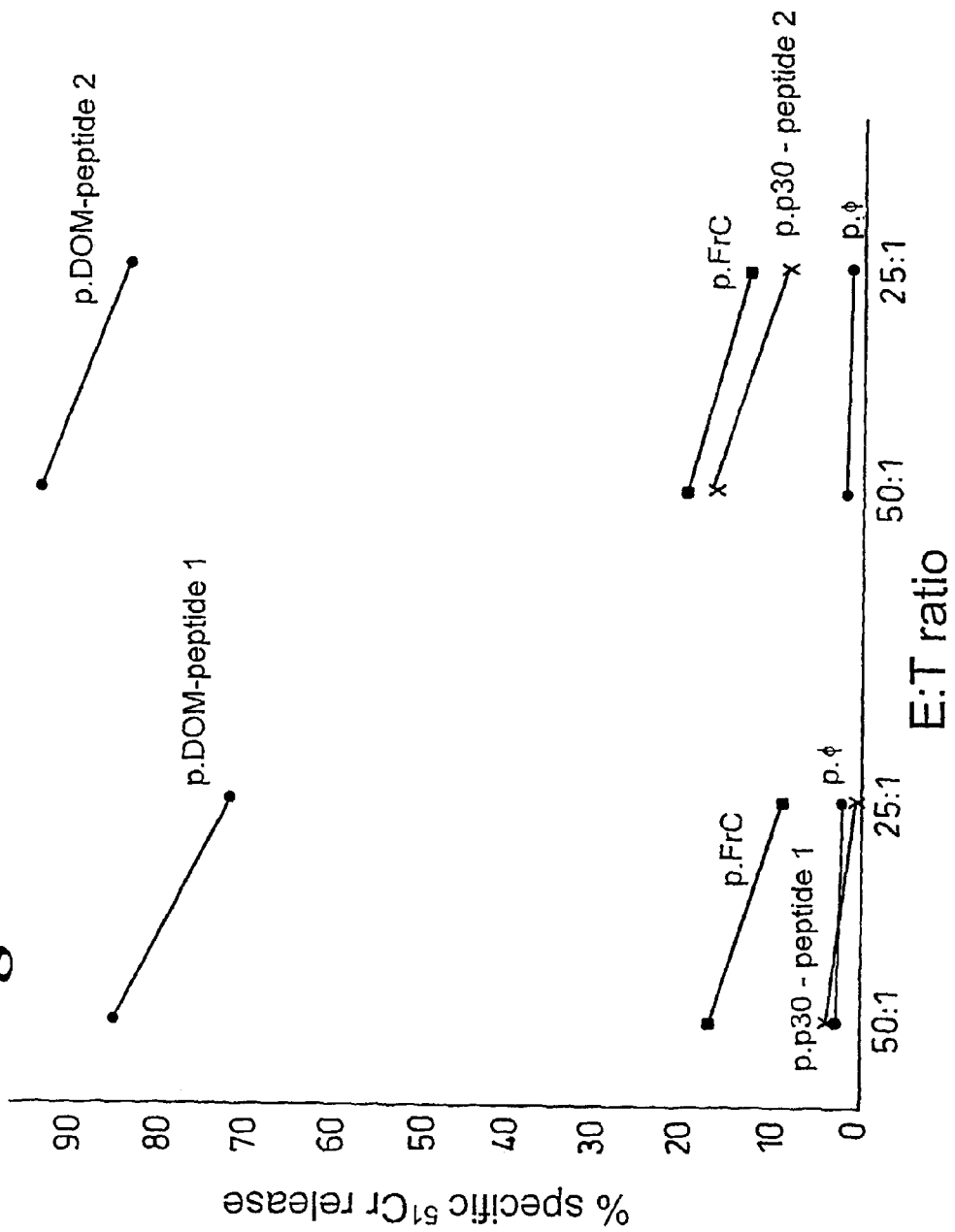

FIG. 9 shows repositioning peptides 1 or 2 from the embedded site in the second domain to the C-terminus of the first domain of FrC amplifies the specific anti-peptide CTL responses. Vaccination with DNA encoding either full length FrC (p.FrC); or the first domain fused is to peptide 1 or 2 repositioned at the C-terminus (p.DOM-peptide); or the p30 helper epitope of FrC fused to peptide 1 or 2 sequence (p.p30-peptide); or control plasmid containing no insert (p.φ), was carried out. At day 14, splenocytes were restimulated with peptide 1 (left side) or peptide 2 (right side), prior to measuring CTL activity by a $^{51}$Cr-release assay using peptide-loaded EL4 target cells. Lysis of target cells loaded with control peptide was negligible in each case (less than 2.2%).

FIG. 10 shows the comparison of the abilities of DNA vaccines containing embedded or repositioned peptides to induce CD8+ T cells containing intracellular IFNγ. Vaccination with DNA encoding either full length FrC (p.FrC); or the first domain fused to peptides 1 and 2 repositioned at the C-terminus (p.DOM-peptide); or p30 helper epitope fused to peptide 1 or 2 sequence (p.p30-peptide), was carried out. At day 14, splenocytes were restimulated with peptide 1 or peptide 2 as indicated, and the percentages of CD8+ T cells containing intracellular IFNγ are indicated. The relative efficiencies of the constructs paralleled the $^{51}$Cr release assays (FIG. 9).

FIG. 11 shows the ability of CTLs induced by DNA vaccines containing p.DOM-peptide sequences to kill target transfectants. Following vaccination with p.DOM-peptide 1 (a and b) or p.DOM-peptide 2 (c and d), splenocytes were taken at day 14 and restimulated with peptide, for 6 days in vitro, prior to testing for activity against $^{51}$Cr-labeled target cells. Target cells included: EL4 cells transfected with leaderless FrC (□) or with empty vector (■); EL4 cells alone (▲) or loaded with peptide 1 (◇) or peptide 2 (○).

FIGS. 12*a* and *b* shows a comparison of the abilities of DNA vaccines containing embedded or repositioned peptide 1 to induce protective immunity against challenge with EL4-FrC transfected tumor cells. Vaccination with DNA encoding either full length FrC (p.FrC); or the first domain fused to peptide 1 or peptide 2 sequence repositioned at the C-terminus (p.DOM-peptide 1 or p.DOM-peptide 2); or p30 helper epitope fused to peptide 1 (p.p30-peptide 1), was carried out on days 0 and 21, using 8 mice per group. At day 28, $10^5$ tumor cells were injected sc, and mice were sacrificed when tumor size reached 1.5 cm diameter.

FIG. 13 shows the ability of the p. DOM-peptide design to induce a CTL response against a candidate peptide from carcinoembryonic antigen (CEA). Vaccination with DNA encoding DOM with a sequence encoding the EAQNTTYL (SEQ ID NO: 4) peptide from CEA fused to the C-terminus. At day 14, splenocytes were restimulated with peptide and tested: a) in a $^{51}$Cr-release assay using target EL4 cells loaded with specific peptide (●) or control peptide (○). Mice vaccinated with p.DOM alone were also tested for responses against specific peptide (▲) or control peptide (Δ). In b), a parallel assay of the percentage of responding CD8+ T cells with intracellular IFNγ is shown.

FIG. 14 shows that suppression of the CTL response against a candidate peptide from carcinoembryonic antigen (CEA) using the two-domain FrC-peptide design is overcome by using the p. DOM-peptide design. Vaccination with DNA encoding (a) the first domain of FrC with a sequence encoding the EAQNTTYL (SEQ ID NO: 4) peptide from CEA fused to the C-terminus (p.DOM-$CEA_{526-533}$), (b) DNA encoding the first domain of FrC alone (p. DOM), (c, d) DNA encoding the full length FrC with the sequence encoding the EAQNTTYL (SEQ ID NO: 4) peptide fused to the C-terminus (p.Frc-$CEA_{526-533}$). At day 14, splenocytes were restimulated with $CEA_{526-533}$ (a to c) or peptide 1 (d), for 6 days in vitro, prior to measuring CTL activity by a $^{51}$Cr-release assay using EL4 target cells loaded with either $CEA_{526-533}$ peptide (▲) or peptide 1 (■).

FIG. 15 compares the abilities of the two domain FrC-peptide design and the p. DOM-peptide design to induce CD8+ T cells containing intracellular IFNγ. Vaccination with DNA encoding (a) the first domain of FrC with a sequence encoding the EAQNTTYL (SEQ ID NO: 4) peptide from CEA fused to the C-terminus (p. DOM-$CEA_{526-533}$), (b) DNA encoding the first domain of FrC alone (p. DOM), (c and d) DNA encoding the full length FrC with the sequence encoding the EAQNTTYL (SEQ ID NO:4) peptide fused to the C-terminus (p. FRc-$CEA_{526-533}$). At day 14, splenocytes were restimulated with peptide $CEA_{526-533}$ (a to c) or peptide 1 (d), for 6 days in vitro, prior to FACS analysis: the percentages of CD8+ T cells containing intracellular IFNγ are indicated. The relative efficiencies of the constructs paralleled the $^{51}$Cr-release assays (FIG. 14).

Table 1 shows the PCR primer sequences used to construct the DNA vaccines used in the experimental work underlying the invention.

DETAILED DESCRIPTION

Strategies for activating immunity against cancer are now under intensive investigation. DNA vaccination offers a relatively simple route between identification of genetic changes in tumour cells and preparing a test vaccine. However, the way in which the encoded protein gains access to the machinery of antigen presentation and to activation of effective immunity is not yet completely clear. Injected muscle cells do not appear to present antigen directly to T cells (1,2), but are likely to act as a reservoir of antigen for indirect presentation (2). Direct transfection of antigen presenting cells (APCs) may occur from the muscle site (3), but only at very low levels (4,5). There is also the question of which effector pathway will be most efficient in attacking the tumor cell, and this obviously depends on the nature of the expressed antigen.

Preceding this invention, DNA vaccines were being developed to treat B-cell malignancies, using as the target antigen the idiotypic (Id) determinants of the clonotypic Ig, encoded by the variable region genes $V_H$ and $V_L$ (6,7). For lymphoma, anti-Id antibody is effective in killing tumour cells (6, 8, 9), therefore the DNA vaccine was designed to induce antibody. Initially, a vaccine containing the $V_H$ and $V_L$ genes assembled as single chain Fv alone (10) proved ineffective in inducing anti-Id in mouse models (11). Fusion of a gene encoding the Fragment C (FrC) of tetanus toxin to the scFv sequence led to strong promotion of antibody production, with protection against lymphoma challenge (12,13). This design is now being tested in a pilot clinical trial of patients with low grade follicular lymphoma. The requirement for fusion of genes encoding additional proteins, such as xenogeneic protein (14) or chemokines (15), in order to engage the immune response against Id antigens has been a general finding. In the present case, the fact that fusion was an absolute requirement, with separate plasmids having no promotional effect supported the concept that the FrC-specific T cells may be providing help to B cells secreting anti-Id (12). Interestingly however, the same scFv-FrC design was able to induce protective immunity against an Ig-secreting, surface Ig-negative myeloma model, apparently mediated by effector T cells (13), likely to be of the CD4+ subset (16).

Although this design may be suitable for surface or secreted target antigens, many candidate tumour antigens are intracellular, and will be presented only as peptides in association with MHC Class I molecules (reviewed in 17). The question then is whether fusion with FrC sequence would be necessary or useful for inducing CTL-mediated immunity against candidate tumour-derived peptides. The inventors had already found that FrC itself, when delivered as a DNA vaccine, was able to induce a CTL response, and an $H2-K^b$-restricted peptide motif had been identified at position 1287-94 in the FrC sequence (13,18). The phenomenon of immunodominance, where CD8+ T cells focus on only one or a few peptide motifs, is clearly evident in responses to viral infection (19). In fact, immunodomination has been described as a central feature of CD8+ T-cell responses (reviewed in 20). If this is the case for DNA vaccines, it would argue against fusing potentially competing FrC sequence to the tumour peptide sequence.

FrC is composed of two domains, a jelly roll N-terminal domain and a second β-trefoil domain (21). The first domain contains a well described "universal" helper epitope, p30 (22,23), which binds to a range of mouse and human MHC Class II alleles, and is recognized by CD4+ T cells (24). Previously, the inventors identified an epitope involved in inducing CD8+ T cells in the second domain (18). They have identified a further epitope with a similar ability to induce CD8+ T-cell responses, also in this domain. The inventors have now investigated two factors which may be important for induction of CTL responses against candidate epitopes presented via DNA: first the position of the peptide epitope in the DNA sequence; second the role of the domain containing the helper epitope in promoting CTL activity.

To test the relevance of the induced CTLs for attacking cancer cells, the inventors have transfected full length FrC into EL-4 cells, where processed peptides can act as surrogate target antigens. To move closer to cancer, the inventors have also demonstrated that a vaccine of similar design, incorporating a known epitope from carcinoembryonic antigen, induced high levels of specific CTL. Using this model, the requirement to remove potentially competing epitopes from the adjuvant FrC sequence was validated.

Results

Production of ΔFrC

A nucleic acid sequence was assembled comprising a first part that encodes the first domain of FrC and a second part which encodes a peptide known to induce cytotoxic T-cell responses. In this particular example, the peptide is contained within second domain of FrC. However, it is representative of a peptide comprising cytotoxic T-cell motifs.

The assembly of the nucleic acid construct is carried out as outlined in FIG. 3 using a plasmid backbone such as pcDNA3 (Invitrogen7) (FIG. 3). In brief, the starting plasmid comprises the entire FrC and a leader sequence (FrC+L). The 5' leader sequence is derived from a tumour (BCL1). This starting plasmid is called pFrC+L.

Primers are then used to isolate the first domain of FrC (ΔFrC) as shown in part 2 of FIG. 3. The PCR product is then cleaned, digested to remove unwanted nucleic sequence, for example introduced from the primers, and cloned back into pcDNA3 using HindIII and NotI sites. The resulting plasmid thus contains the first domain of FrC only fused to a leader sequence (BCL1), with a stop codon added at the end of this FrC first domain.

Production of ΔFrC Plus Peptide Antigen

In order to introduce a disease antigen into the plasmid, a reverse primer at the 3' end of ΔFrC also coding for the disease antigen in question is used to add this sequence to the ΔFrC sequence. This is shown diagrammatically in part 3 of FIG. 3.

For disease antigens that are contained on longer peptide sequences, a PCR Soeing technique is used with overlapping primers.

FIGS. 2 and 4 to 6 show details of the vectors pcDNA3 and pVAC1 which are examples of the sort of vectors which can be used in accordance with the present invention to carry the nucleic acid construct. The present inventors have found that it is preferable to replace the RSVLTR with a promoter sequence from cytomegalovirus (pCMV).

Identification of CTL-Inducing MHC Class I Binding Motifs in FrC

The amino acid sequence of FrC was scanned for peptide 8-mer motifs with potential for binding to or $H2-K^b$ or $H2-D^b$ (31). Using an algorithm to assign a score based on the estimated half time of dissociation of a molecule containing this sequence (31), 8 peptides with values of >13 for binding to $H2-K^b$ were identified and synthesized. The top 20 predicted binding sequences gave values ranging from 86.4 to 1.32. Known immunodominant $K^b$-restricted CTL epitopes score between 132 (RGYVYQGL; SEQ ID NO: 5) and 17 (SIINFEKL; SEQ ID NO: 6) The $K^b$-binding Sendai virus nucleoprotein derived sequence FAGNYPAL (SEV; SEQ ID NO: 7) scored 60, while a control, $D^b$-restricted epitope (ASNENMDAM; SEQ ID NO: 8) scored 1. FrC sequences which scored <8, including the only $H2-D^b$-binding candidate, were not investigated further.

Figure 8A:
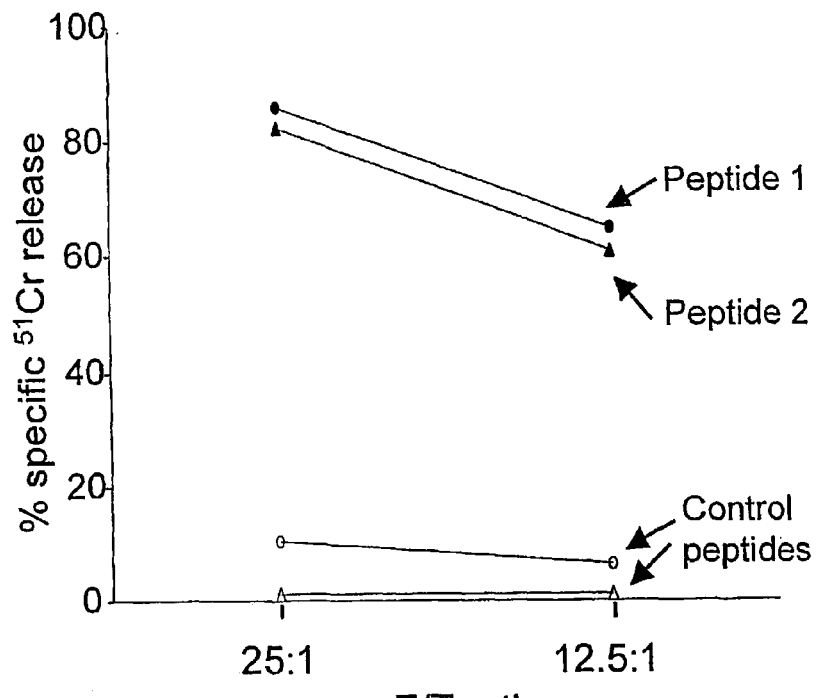

Mice were then vaccinated with the DNA vaccine containing the gene encoding full length FrC (p. FrC). At day 14 after one vaccination, CTL responses against peptide-loaded EL4 cells could be detected using 2 of the 8 peptides following. one restimulation in vitro (FIG. 8a). Further injections, or additional restimulations in vitro, failed to elicit CTL responses to the remaining 6 candidate peptides. The two positive peptides, which the inventors have termed peptide 1 and peptide 2, were derived from the second domain of FrC, sited at positions 1287-94 and 1162-69 and respectively.

Figure 8B:
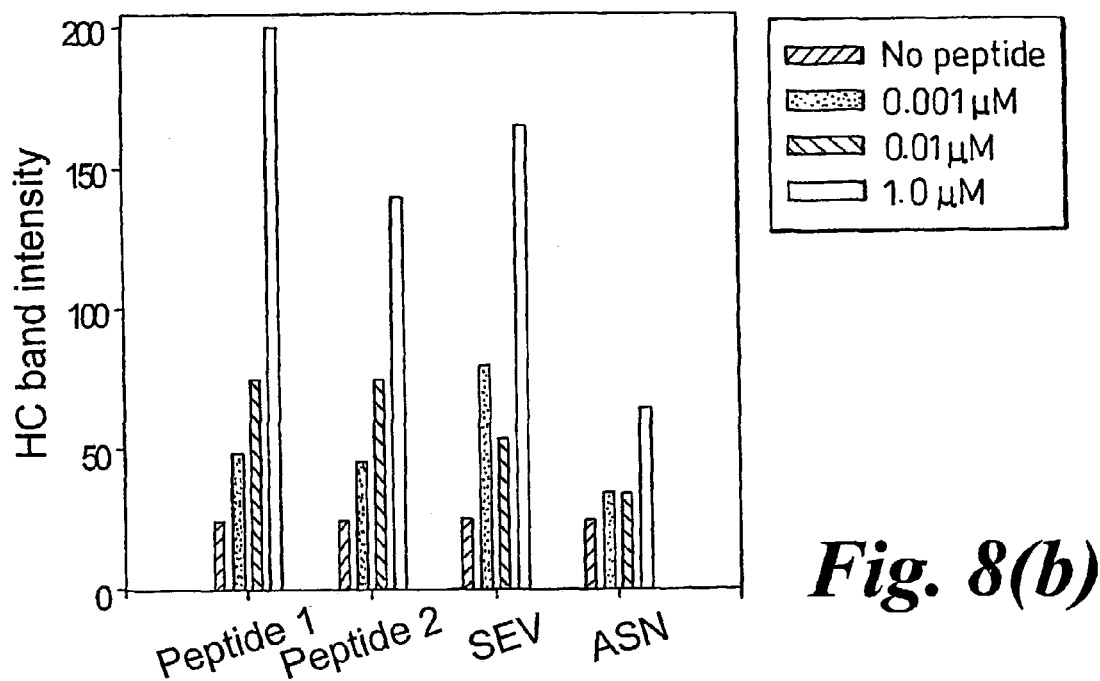

The remaining peptides were unable to stimulate any detectable CTL activity. Interestingly, of the two immunostimulatory peptides, peptide 1 (SNWYFNHL; SEQ ID NO: 2) had the lowest score (13.2) and peptide 2 (LNIYYRRL; SEQ ID NO: 3) was ranked third, with a score of 26.4. In an in vitro binding assay, both peptide 1 and peptide 2 were able to bind to H2-$K^b$ equally well, and not significantly differently to the positive control peptide SEV (FIG. 8b). Thus, although the predictive algorithm was successful in identifying both immunostimulatory sequences, there may be poor correspondence between predicted binding and the actual ability to bind to class I and stimulate a CTL response as has been noted before (32).

Effect of Repositioning the Peptide Sequences to the C-Terminus of the First Domain Peptides 1 and 2 were able to induce CTL responses following vaccination with full length FrC sequence, but the response was relatively weak, with two restimulations required to produce high levels of $^{51}Cr$ release. Since tumour antigens may also have low immunogenicity, the inventors used these peptides as models to improve immunogenic activity via DNA delivery. They investigated first the effect of removing the peptide sequences from the FrC backbone and repositioning them at the C-terminus of the first domain (p.DOM). A single intramuscular injection with p.DOM-peptide 1 or p.DOM-peptide 2 generated rapid high level CTL responses detectable after one stimulation in vitro. Comparison with the original p.FrC vaccine is shown in FIG. 9, and similar results were obtained in multiple experiments.

Cytolytic activity was paralleled by the levels of intracellular IFNγ found in the CD8+ T-cell population (FIGS. 10a and b), with the p.DOM-peptide vaccines regularly inducing x2-3 fold increases in the percentages of IFNγ-positive CD8+ cells, as compared to the p.FrC vaccine. The CTLs were also able to lyse EL4 cells transfected with leaderless p.FrC (FIG. 11), with those specific for peptide 1 being more effective. This indicates that the CTLs induced by peptide 1 are more able to kill the target transfectants than those induced by peptide 2. The reason for this is unclear at present but it may mean that not all candidate peptides are useful as targets.

Although only low levels of specific lysis were observed for CTLs against peptide 2, these were consistent in repeated experiments. In contrast, no significant lysis of EL4 cells transfected with empty vector was observed. Addition of peptide to the target cells clearly increased specific lysis, indicating that the transfectant was able to process and present only low levels of both peptides by the endogenous route (FIG. 11). However, levels of expression were sufficient for effector CTLs specific for either peptide 1 or 2 to attack the transfectant in vivo (see below).

Contribution of Domain 1 (p.DOM) to CTL Induction Via DNA Vaccination

Figure 10:
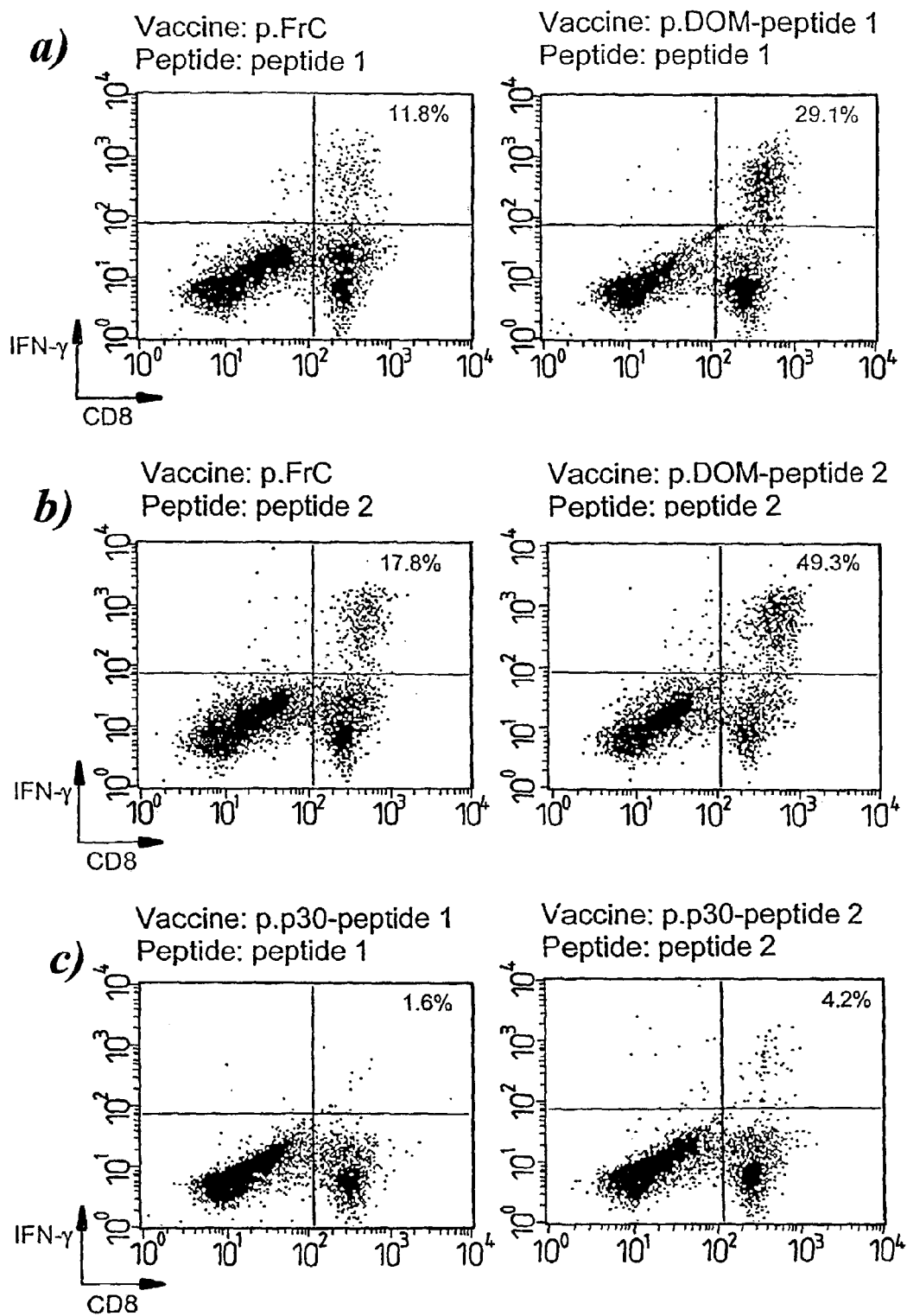

Domain 1 contains one identified "universal" peptide at position 947-967 which can be recognized by human T cells (24) or mouse T cells (33) in association with a large number of MHC Class II molecules. Since this could be a critical component of p.DOM for provision of T-cell help (34), the inventors investigated its role in CTL induction. They compared the ability of a DNA vaccine containing only the p30 sequence linked to each of the CTL peptide sequences with that of p.DOM-peptide vaccines. FIG. 9 shows that p.p30-peptide 1 was poor in inducing a CTL response; p.p30-peptide 2 was more effective, but it performed considerably less well than p.DOM-peptide 2, and was in fact less effective than the original p.FrC vaccine. A comparison of the numbers of CD8+ T cells producing intracellular IFNγ showed the same trend (FIG. 10c). Repeated vaccination and restimulations with the p.p30-peptide vaccines could generate CTLs (data not shown) confirming the integrity of the constructs, but indicating their inferior performance. The conclusion is that p.DOM contains additional sequence information required for induction of an effective CTL response against attached peptides.

Contribution of p.DOM to CTL Induction via Peptide Vaccination

The inventors then investigated whether the adjuvant effect of p.DOM on CTL induction via DNA delivery was apparent when administered with synthetic peptides. Peptide 1 was mixed with p.DOM, and injected into muscle.

However, no CTL activity was induced, even following three injections at days 0, 21 and 42, and up to 4 weekly restimulations in vitro (data not shown). It appears that fusion of p.DOM to the peptide sequence is required, either for delivery to the same cell, or to ensure that synthesis of the first domain and the presence of the peptide are coincident.

Protection

Figure 12A:
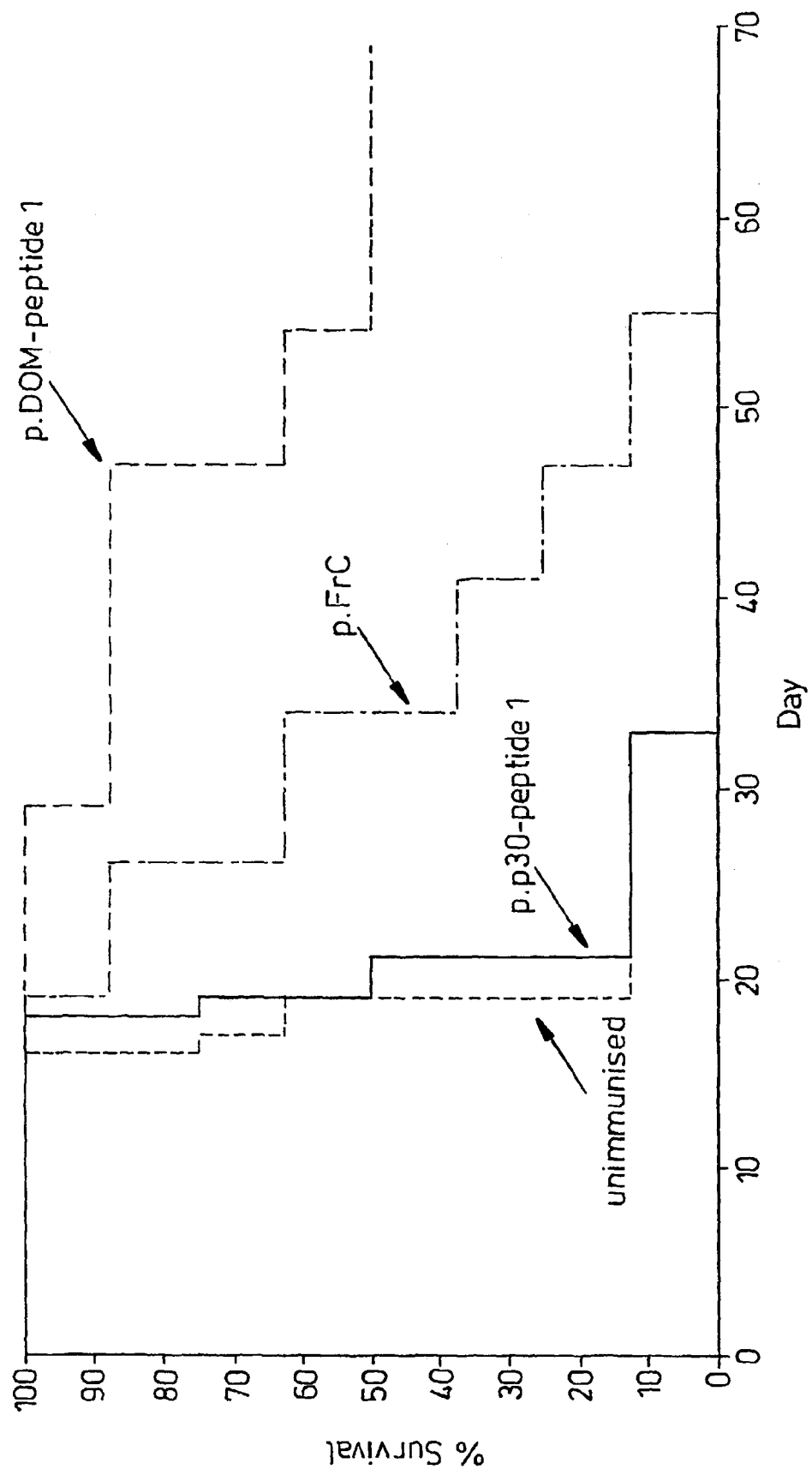
Figure 12B:
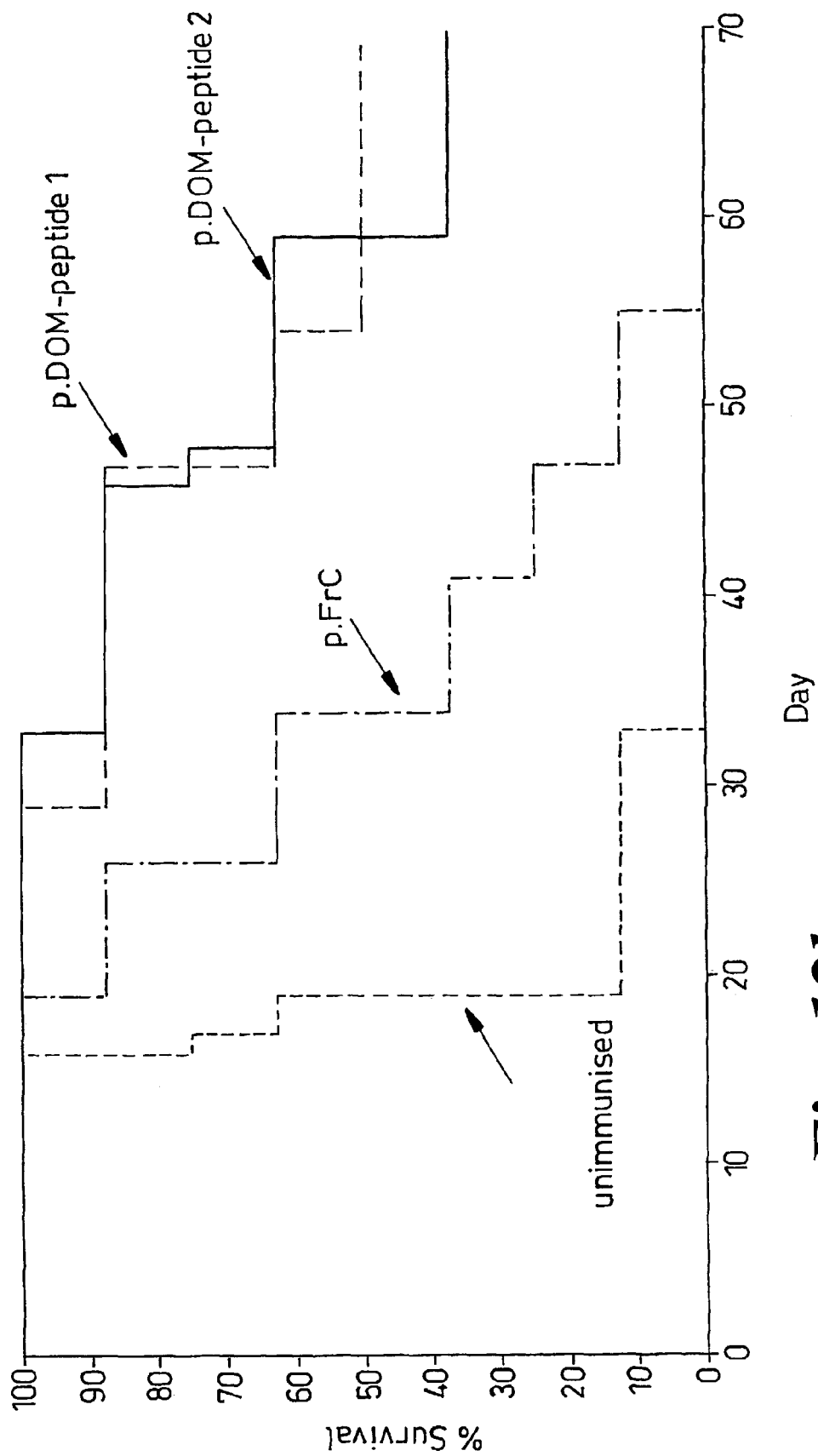
Figure 13:
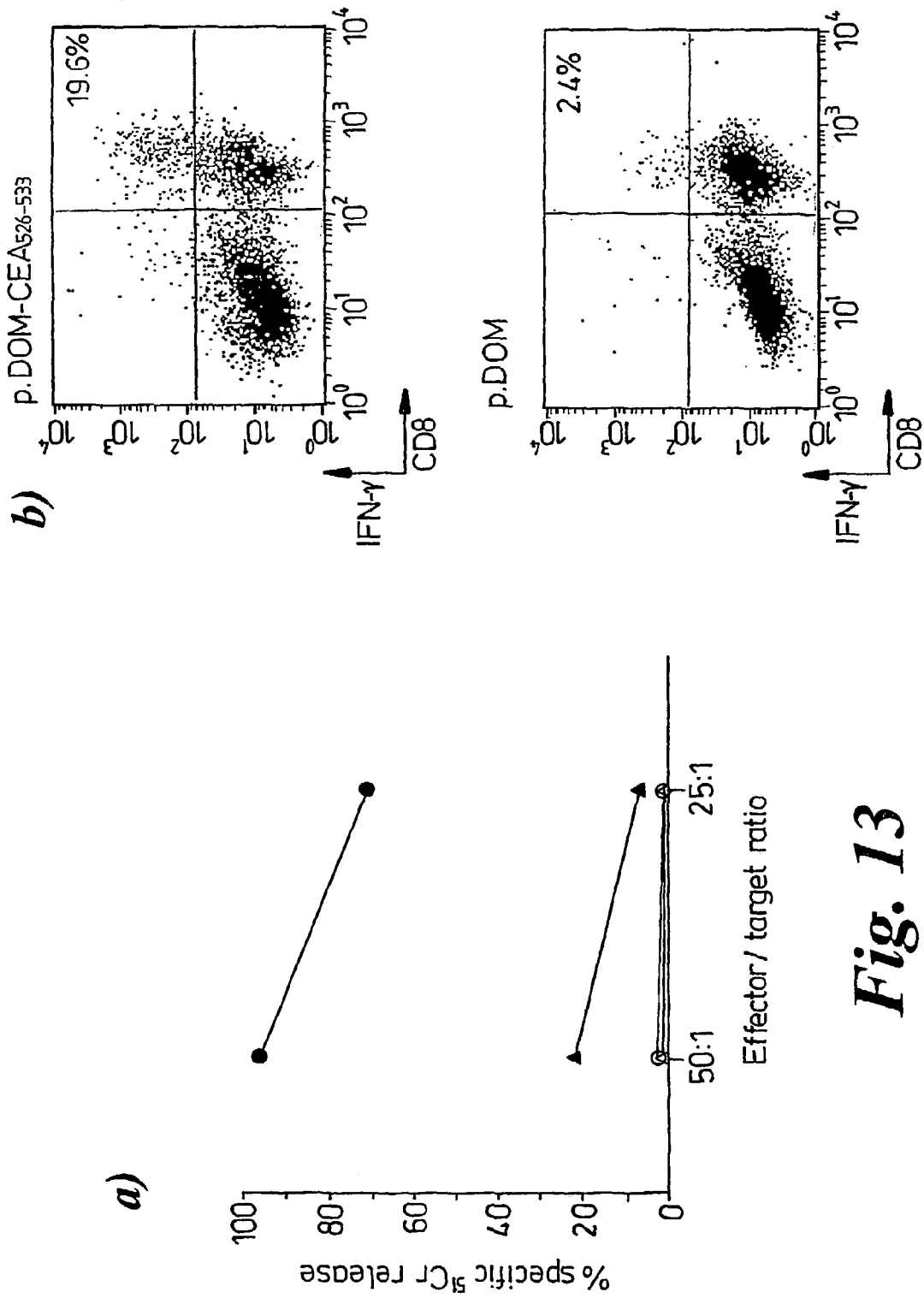

Vaccination at day 0 and day 21 with p.DOM-peptide 1 led to significant protection against challenge with the EL4-FrC transfectant at day 28 (FIG. 12), with no effect on growth of EL4 cells transfected with empty vector (pcDNA3) (data not shown). At this relatively early time of challenge (day 28), p.DOM-peptide 1 was superior to the full length p.FrC plasmid, consistent with the rapid induction of CTLs. However, although the p.FrC vaccine failed to generate sufficient CTLs by day 14 to kill the transfectant in vitro after one restimulation, some protection was evident (FIG. 12), likely due to expansion of CTLs by the second injection. CTLs able both to kill the transfectant in vitro and to protect against challenge could be induced by the 2-domain p.FrC after a third vaccine injection (data not shown). Vaccination with the plasmids containing only the p30 helper epitope fused to either peptide 1 or 2 sequence was completely ineffective in providing protection (FIG. 12), as expected from the poor ability to induce CTLs (data not shown). Depletion experiments showed that all protection was abrogated by depletion of CD8+ T cells (data not shown). Depletion of CD4+ T cells could not be carried out due to expression of CD4 by EL4 cells. These results indicate that the CTLs induced by the repositioned peptide 1 are contributing to protection against tumour.

p.DOM-peptide Design to Induce CTLs Against a Peptide from Carcinoembryonic Antigen To test the ability of the p. DOM-peptide design to induce CTLs against a candidate tumor-associated antigen, a peptide derived from carcinoembryonic antigen (CEA) was chosen. Peptide EAQNTTYL (SEQ ID NO: 4) is known to act as a target for CTLs induced by vaccination of B6 mice with recombinant vaccinia virus (35). The encoding sequence was placed at the 3'-end of first domain to make the peptide vaccine (FIG. 7). This was injected into mice and CTL activity measured on day 14 after one restimulation in vitro. A high level of CTL activity was induced (FIG. 13a) with ~20% of IFNγ-containing CD8+ T cells (FIG. 13b). The control p.DOM plasmid alone produced a low level of CTL activity and a few (2.4%) CD8+ T cells (FIG. 13b).

Evidence for Epitopic Competition

Figure 14:
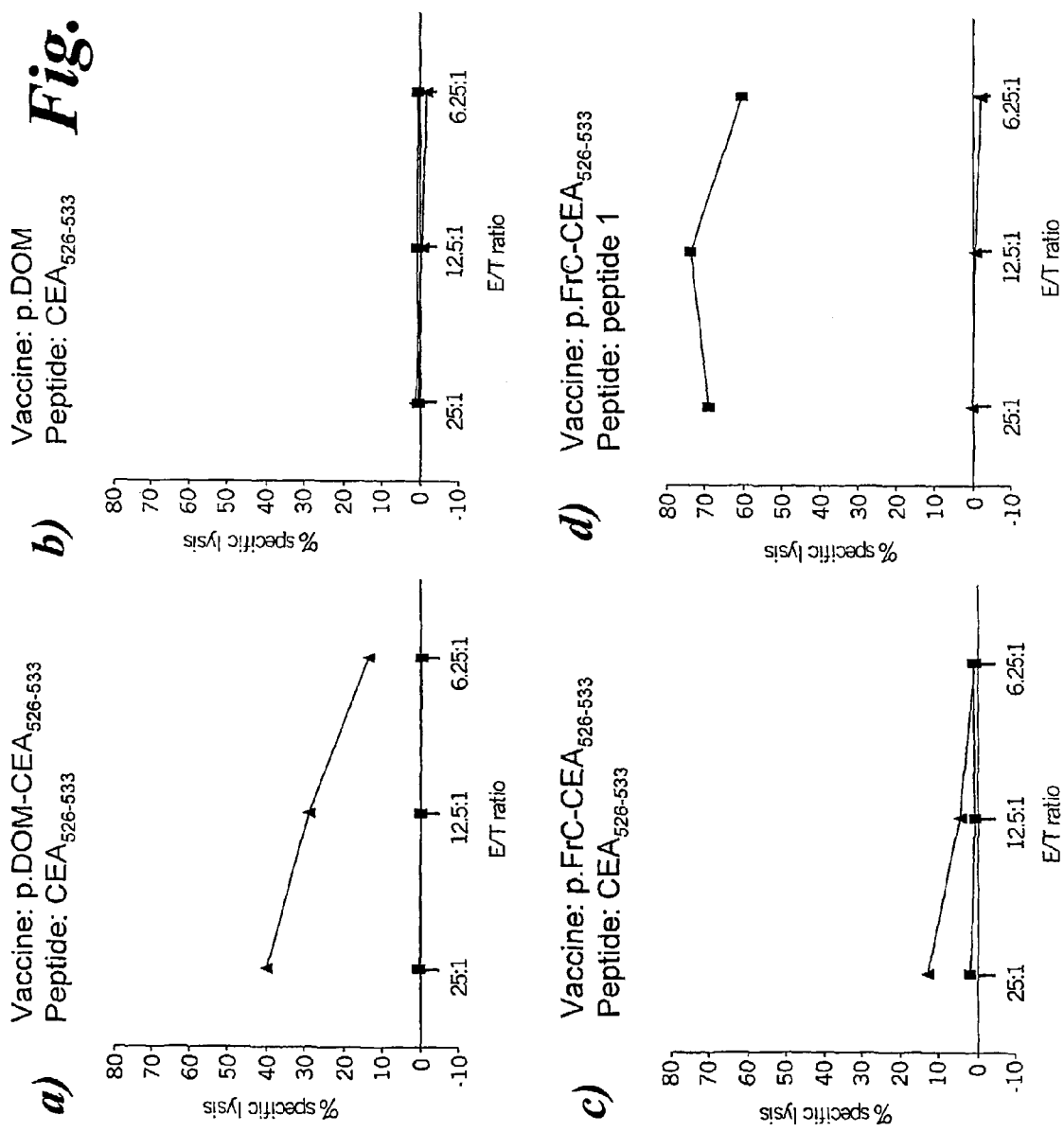

The CEA model was used to investigate the assumption that epitopes in the second domain of FrC would compete with attached tumor-derived epitopes. The CEA peptide sequence was placed at the carboxyl end of the 2-domain (full length) FrC sequence to produce p.FrC-$CEA_{526-533}$ (FIG. 7). The ability of this construct to induce CEA-specific CTLs was then compared with that of the single domain p.DOM-$CEA_{526-533}$ design, using one injection and one restimulation in vitro. In repeated experiments, the single domain vaccine induced x2-3 fold higher levels of CTL activity against the CEA epitope (FIG. 14a) as compared with the construct containing 2-domain FrC (p.FrC-CEA$_{526-533}$) (FIG. 14c). However, the 2-domain construct was able to induce high levels of CTL activity against the FrC peptide 1 (FIG. 14d). This strongly suggests that inclusion of potentially competitive epitopes within the second domain of FrC leads to suppression of induction of CEA-specific CTL activity.

Figure 15:
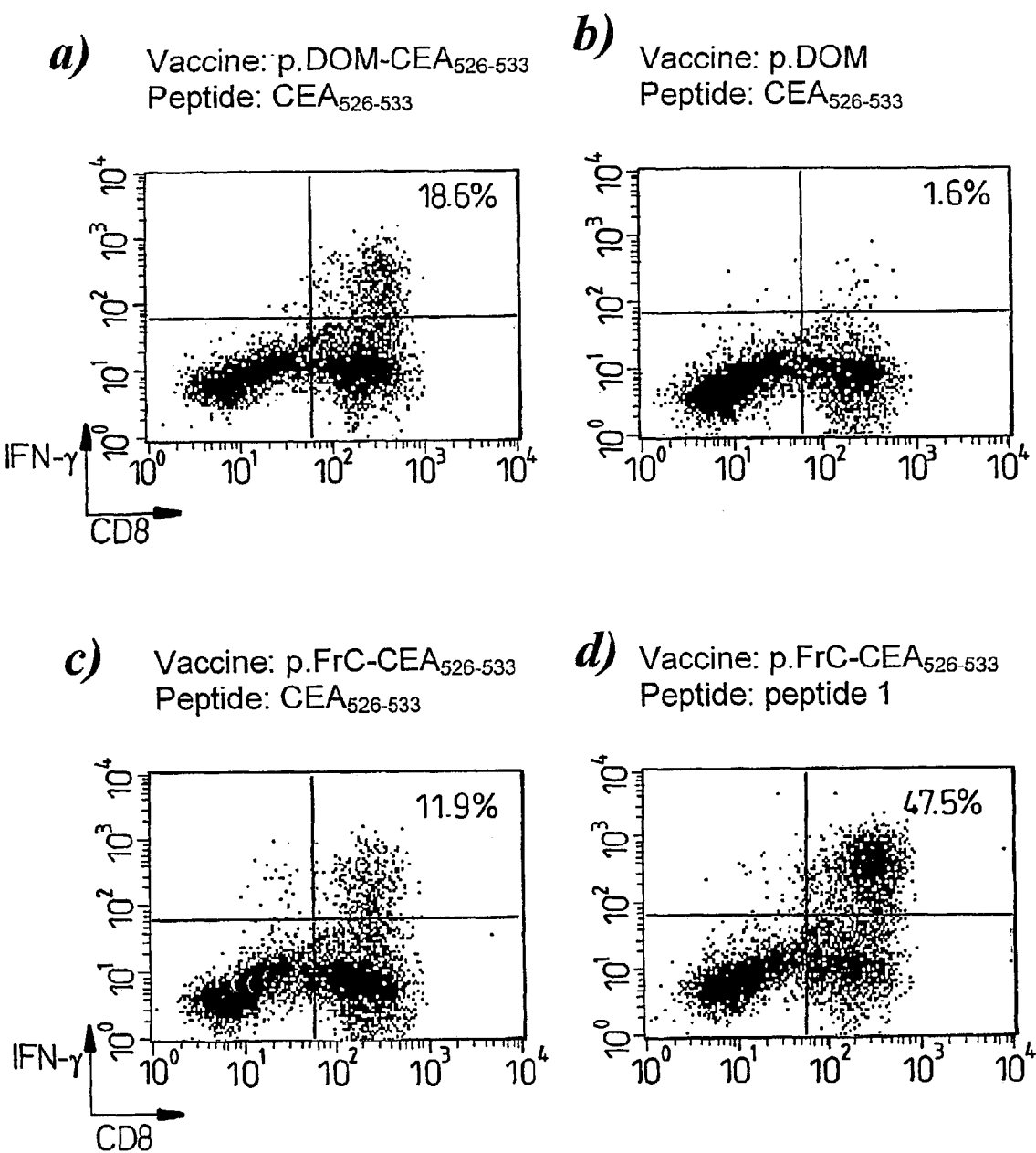

Cytolytic activity against CEA peptide was paralleled by the levels of intracellular IFNγ found in the CD8+ T-cell population, with the p.DOM-CEA$_{526-533}$ vaccine inducing 2-3 fold higher levels of IFNγ-positive cells, as compared to the 2-domain vaccine (FIGS. 15a and 15c). As expected, the induction of high levels of CTL activity against peptide 1 of the second domain of FrC was mirrored by high levels of IFNγ-positive CD8+ T cells (FIG. 15d). The control p.DOM vaccine produced no significant CTL activity (FIG. 14b) and very low levels of IFNγ-positive CD8+ T cells (FIG. 15b).

These results confirm the anticipated advantage of removing the second domain of FrC on induction of the response to the CEA epitope, and suggest that the p.DOM-peptide design may have general application for tumor antigens.

Discussion

Successful vaccination against cancer is likely to require activation of multiple pathways of immunity, including CTLs. Although DNA vaccines are efficient in inducing CTL responses (36), tumor antigens are often weak (12), and deletion of high affinity CD8+ T cells may have occurred (37). To generate CTLs, candidate peptides should be processed and presented efficiently by the APCs, preferably in the absence of competing peptides which could override the response (reviewed in 20). The inventors have investigated CTL responses against the FrC sequence of tetanus toxin, first because of their interest in using FrC as an adjuvant "foreign" sequence to activate immunity against attached scFv sequence (12).

Using their DNA scFv-FrC vaccines against a mouse B-cell lymphoma and myeloma, protective anti-Id immunity is promoted, involving antibody and CD4+ T cells respectively (13). CTL responses were not detected against scFv, possibly due to a lack of MHC Class I-binding motifs within the V-genes. However, CTLs were induced against two peptide motifs in the second domain of FrC (13,18). While responses were relatively weak, they have the potential to compete with CTL motifs from attached tumour sequences (38). In order to investigate the adjuvant potential of FrC sequence for inducing CTLs against candidate peptides, the inventors removed the second domain, leaving the first domain to provide T-cell help via the "universal" peptide p30 (24,34).

Operation of the first domain (p.DOM) as an adjuvant was then tested using the two peptide motifs from the second discarded domain. Repositioning to the C-terminus of p.DOM led to a striking increase in CTLs against each peptide. The inventors found previously that CTLs against FrC are induced more efficiently if the leader sequence is present (18), and consequently they have included the leader in all the constructs described here. Inclusion of the leader sequence should ensure that all constructs longer than around 60 amino acids are co-translationally transported into the ER. The effect of repositioning may then reflect the "C-end rule", whereby antigenic peptides are preferentially produced from the C-terminus of precursor peptides or proteins in the ER site (39). This could also be relevant for indirect transfer of peptides from muscle to APCs via heat shock proteins such as gp96 or calreticulin, which are normally resident in the ER (40).

The second investigation was to assess the contribution of p.DOM to induction of CTLs against attached peptide sequence. In a model system, a DNA vaccine encoding the immunogenic $K^b$-restricted epitope of OVA (SIINFEKL; SEQ ID NO:6), fused to the adjacent I-$A^b$-restricted helper peptide sequence was able to induce CTLs (34). This indicates that a helper epitope and a CTL epitope might be the only requirements. In this particular case, this design was insufficient, since a fusion gene encoding the "universal" helper peptide sequence fused to either of the CTL epitopes generated only low levels of CTL activity. This may be due to the relative weakness of the FrC-derived peptides, as compared to the OVA peptide, but it may indicate a problem for tumour antigens. Another possibility relates to the important contribution of the leader sequence to the immunological potency of these DNA vaccines. The supply of shorter constructs to the ER may be poor since these will depend on rather than co-translational transport (41) which is less efficient and may therefore give rise to less efficient priming. It is nevertheless likely that additional sequences in p.DOM either provide more T-cell help, or contribute to peptide presentation by other mechanisms. One possibility is that the 25 KD domain increases the level of the attached peptide by protecting it from degradation in the cytosol. A further possibility is that the presence of some mis-folded FrC domain in the ER may influence loading of attached peptides onto heat shock proteins for cross-priming (42).

The finding that p.DOM-peptide 1 activates a rapid CD8+ T-cell-mediated protective immunity against the EL4-FrC tumour, and appears more efficient than the vaccine containing full length FrC (p.FrC) indicates two features with relevance for cancer therapy. The first is that repositioning can increase the effectiveness of a vaccine aimed to induce peptide-specific CTLs. Obviously the peptide chosen must also be presented by the tumour cell, but levels required for effector cell recognition can be low (20). The second is that p.DOM can provide activating signals required for DNA vaccines against weak peptide antigens. Interestingly, 4/6 candidate HLA-A2-binding motifs are also in the second domain of FrC, and early studies have shown that the highest functional levels are also in that sequence (unpublished observations). The inventors' data using the known CEA-derived peptide sequence indicate that the p.DOM-peptide design may be applicable to other cancer antigens. Using this model, it was also possible to demonstrate the advantage of removing the second domain of FrC, since potentially competitive epitopes within that domain were able to depress induction of CEA-specific CTLs. This finding confirms the principle behind the design. The fact that the first candidate peptide from CEA generates a rapid and high level of CTLs from this format is encouraging and the results show that the p.DOM strategy has relevance for human vaccines.

Materials and Methods

Construction of DNA Vaccines

Construction of the DNA vaccine (p.FrC) containing the gene encoding the full length two domain sequence of FrC (amino acids 865-1315 of tetanus toxin (TT$_{865-1315}$)), with a leader sequence derived from the V$_H$ of the IgM of the BCL$_1$ tumour has been described (25,26). The DNA vaccine containing the gene encoding the first domain (21) (p.DOM) was constructed by PCR amplification of the amino terminal domain sequence (TT$_{865-1120}$) from p.FrC using the forward and reverse primers FrCf1 and FrCr1 respectively (Table 1), prior to cloning into pcDNA3. This plasmid was then used as template for the construction of three similar vaccines, each including the first domain but with a distinct CTL epitope sequence fused to the carboxyl terminus. Assembly of p.DOM-peptide 1, encoding the $TT_{1287-1294}$ peptide; p.DOM-peptide 2, encoding the $TT_{1162-1169}$ peptide; or p.DOM-CEA, encoding the $CEA_{526-533}$ peptide, was identical to that of p.DOM alone, except that a different reverse primer was used in each case (FrCr2, FrCr3 and FrCr4 respectively) which overlapped with the p.DOM carboxyl sequence and incorporated the CTL epitope sequence of interest. The DNA vaccine $p.FrC-CEA_{526-533}$ was constructed by PCR amplification of the full length FrC sequence using the forward primer FCf1, together with primer FCr5, which overlaps the 3' sequence of FrC and encodes the CEA CTL epitope ($CEA_{526-533}$), fusing it to the carboxyl terminus of FrC. The PCR product was then cloned into pcDNA3.

p.p30-peptide 1 was assembled by linking the DNA sequence encoding the CTL epitope $TT_{1287-1294}$ to that encoding a "universal" T helper epitope, p30 ($TT_{947-967}$), located in the first domain of FrC (24). A three step PCR assembly procedure was used: first, the $BCL_1$ leader sequence was amplified from p.FrC using the forward primer PCMVf1, together with the reverse primer $BCL_1r1$ containing p30 overlapping sequence. Secondly, p30 was amplified from p.FrC with the forward primer p30f1 and the reverse primer p30r1 containing an overhang encoding the CTL epitope $TT_{1287-1294}$. Thirdly, these two gel-purified PCR products were combined and assembled by PCR-SOeing using primers PCMVf1 and p30r1. The vaccine p.p30-peptide 2 was assembled in a similar manner using the reverse primer p30r2 containing an overhang encoding the CTL epitope $TT_{1162-1169}$. All assembled vaccine PCR products were ligated into the expression vector pcDNA3 (Invitrogen Corp., San Diego, Calif.) using Hind III and Not I restriction sites. Primer sequences are shown in Table 1.

The structures of the DNA vaccines are indicated in FIG. 7. Integrity of all constructs was confirmed by DNA sequencing. Expression and size was checked in vitro using the $TNT^R$ T7 Coupled Reticulocyte Lysate System (Promega Corp., Madison, Wis.). Expression in mammalian cells was tested by transfecting COS cells, and measuring FrC-containing protein in the supernatant by ELISA (12).

Peptides

Fragment C (FrC) peptides were synthesized in house on a Shimadzu PSSM8 peptide synthesizer using Fmoc chemistry, and checked for purity by HPLC.

Concentrations were measured by a colorimetric assay (BCA; Pierce, Rockford, Ill.). The coordinates for the $H-2^b$-restricted FrC CTL epitope sequences $TT_{1287-1294}$ (SNWYFNHL: peptide 1; SEQ ID NO: 2) and $TT_{1162-1169}$ (LNIYYRRL; SEQ ID NO:3: peptide 2) correspond to complete Tetanus Toxin (TT) sequence. The $CEA_{526-533}$ peptide (EAQNTTYL; SEQ ID NO:4) has been described previously (27,28). It was synthesized commercially and supplied at >95% purity (Peptide Protein Research Southampton, UK).

Peptide Binding Assay

Binding of each peptide to $H2-K^b$ was performed using the assembly assay as described (29). This assay is based on the observation that, in a detergent lysate of RMA-S cells, $K^b$ molecules are unstable and dissociate after an overnight incubation at 4° C. unless a stabilising ($K^b$-binding) peptide is added at the time of lysis. Only stabilised $K^b$ molecules can therefore be recovered by immunoprecipitation with mAb Y3 after overnight incubation. The amount of recovered $K^b$ is directly proportional to the amount of peptide bound, and the concentration of peptide required to effect 50% maximal recovery represents an approximate binding affinity (29). Recovery of $H2-K^b$ heavy chains (HC) was quantitated after immunoprecipitation and SDS PAGE using AIDA (Fuji).

Vaccination Protocol and CTL Assay

C57BL/6 mice, bred in-house, were vaccinated at 6-10 weeks of age with 50 µg of DNA in normal saline injected into two sites in the quadriceps muscles. For measurement of CTL responses, mice were sacrificed on day 14. Spleens were pooled from vaccinated mice and single cell suspensions were prepared in RPMI medium supplemented with 10% heat-inactivated FCS (Life Technologies, Paisley, UK), 1 mM sodium pyruvate, 2 mM L-glutamine, non-essential amino acids (1% of 100× stock), 25 mM HEPES buffer and 50 µM 2-mercaptoethanol. Splenocytes were resuspended in 40 ml medium, at $3 \times 10^6$ cells/ml, and added to 80 $cm^2$ flasks along with recombinant human IL-2 (20 U/ml, Perkin-Elmer, Foster City, Calif.) and peptide (5-20 µM). T cell cultures were re-stimulated 7 days later in 24-well plates. T cells ($5 \times 10^5$/well) were mixed with irradiated syngeneic 'feeder' splenocytes ($5 \times 10^6$/well), together with rIL-2 (20U/ml) and peptide (5-20 µM). Cytolytic activity of the T cell cultures was assessed 6 days after one in vitro stimulation by standard 4-5 hour $^{51}Cr$-release assays, as previously described (18). For indicated experiments, a further in vitro stimulation was given. Target cells were EL4 cells (ATCC; TIB 39) incubated with a test or control peptide, EL4 cells alone or transfected EL4 cells (see below). Specific lysis was calculated by the standard formula ([release by CTL–release by targets alone]/[release by 4% NP40–release by targets alone]×100%). Spontaneous release by targets alone was always less than 20% of release by 4% NP40.

Intracellular γ-IFN Assay

Viable cells were selected by density centrifugation (Lymphoprep, Nycomed Pharma AS, Oslo, Norway). T cells were incubated for 4 hours at 37° C. in 96U-well plates, at $5 \times 10^5$ cells/well, together with 10U/well rIL-1321 2, 1 µM peptide and 1 µl/well golgiplug (PharMingen). Cells were blocked with 2% decomplemented mouse serum (15 minutes, 4° C.) prior to labeling with 1 µg/well FITC anti-mouse CD8b.2 (Ly-3.2, clone 53-5.8, PharMingen), or an isotype control (20 minutes, 4° C.). Following surface labeling, the cells were fixed with 1% formaldehyde (20 minutes, 4° C.) and then permeabilised with 0.5% saponin (10 minutes, 4° C.) before intracellular labeling with 0.5 µg/well PE rat anti-mouse γ-IFN (clone XMG1.2, PharMingen) for 20 minutes at 4° C. After a final wash the cells were resuspended in PBS and analyzed immediately by FACScalibur, using CELLQUEST software (Becton Dickinson).

Tumor Targets

The inventors have generated a tumour model consisting of EL4 tumor cells into which they have transfected a plasmid encoding a non-secreted (leaderless) form of FrC (18). Briefly, $2 \times 10^6$ cells, in 400 µl medium were mixed with 10 µg plasmid DNA and electroporated at 300V, 975 µF (Gene Pulser Cuvette, 0.4 cm electrode gap, Biorad). The cells were grown in the presence of a selective antibiotic (Geneticin, 2 mg/ml, Life Technologies Ltd.) and, following the restoration of a stable population, were cloned and tested for susceptibility to lysis by FrC-specific CTLs. This led to the generation of the tumour cell line EL4-FrC.

Tumor Challenge

C57BL/6 mice were challenged by subcutaneous injection of $1 \times 10^5$ EL4-FrC transfectants or EL4 cells transfected with empty vector (pcDNA3) into the right flank. Mice were sacrificed when the resulting tumor reached 1.5 cm diameter, in accordance with human endpoints guidelines (UK Coordinating Committee for Cancer Research, London, UK), and the day of death recorded. Cell depletion experiments were performed in vivo by intraperitoneal injection of 100 μg Ig (rat anti-mouse CD8, YTS 169.4.2.1, kindly supplied by Dr. S. Cobbold (30), or an isotype control), every 2-3 days for 14 days, beginning one week before tumor challenge.

The experimental work described herein has also been performed in another strain of mouse (Balb/C), with the same results.

REFERENCES

1. Davis H L, Millan C L, Watkins S C. 1997. Immune-mediated destruction of transfected muscle fibers after direct gene transfer with antigen-expressing plasmid DNA. Gene Ther. 4(3): 181.
2. Corr M, von Damm A, Lee D J, Tighe H. 1999. In vivo priming by DNA injection occurs predominantly by antigen transfer. J Immunol. 163(9): 4721.
3. Chattergoon M A, Robinson T M, Boyer J D, Weiner D B. 1998. Specific immune induction following DNA-based immunization through in vivo transfection and activation of macrophages/antigen-presenting cells. J Immunol. 160(12): 5707.
4. Dupuis M, Denis-Mize K, Woo C, Goldbeck C, Selby M J, Chen M, Otten G R, Ulmer J B, Donnelly J J, Ott G, McDonald D M. 2000. Distribution of DNA vaccines determines their immunogenicity after intramuscular injection in mice. J Immunol. 165(5):2850.
5. Casares S, Inaba K, Brumeanu T D, Steinman R M, Bona C A. 1997. Antigen presentation by dendritic cells after immunization with DNA encoding a major histocompatibility complex class II-restricted viral epitope. J Exp Med. 186(9): 1481.
6. George, A. J. T., and F. K. Stevenson. 1989. Prospect for the treatment of B cell tumors using idiotypic vaccination. Int. Rev. Immunol. 4:271.
7. Eisen H N, Sakato N, Hall S J. 1975. Myeloma proteins as tumor-specific antigens. Transplant Proc. 7(2): 209.
8. George, A. J. T., A. L. Tutt, and F. K. Stevenson. 1987. Anti-idiotypic mechanisms involved in suppression of a mouse B-cell lymphoma, BCL1. J. Immunol. 138: 628.
9. Kaminski, M. S., K. Kitamura, D. G. Maloney, and R. Levy. 1987. Idiotypic vaccination against a murine B cell lymphoma: inhibition of tumor immunity by free idiotypic protein. J. Immunol. 138: 1289.
10. Hawkins, R. E., D. Zhu, M. Ovecka, G. Winter, T. J. Hamblin, A. Long, and F. K. Stevenson. 1994. Idiotypic vaccination against human B-cell lymphoma: rescue of variable region genes from biopsy material for assembly as single-chain Fv personal vaccines. Blood. 83: 3279
11. Stevenson F K, Zhu D, King C A, Ashworth L J, Kumar S, Hawkins R E. 1995. Idiotypic DNA vaccines against B-cell lymphoma. Immunol Rev. 145: 211.
12. Spellerberg, M. B., D. Zhu, A. Thompsett, C. A. King, T. J. Hamblin, and F. K. Stevenson. 1997. DNA vaccines against lymphoma. Promotion of anti-idiotypic antibody responses induced by single chain Fv genes by fusion to tetanus toxin fragment C. J. Immunol. 159: 1885.
13. King C A, Spellerberg M B, Zhu D, Rice J, Sahota S S, Thompsett A R, Hamblin T J, Radl J, Stevenson F K. 1998. DNA vaccines with single-chain Fv fused to fragment C of tetanus toxin induce protective immunity against lymphoma and myeloma. Nat Med. 4(11): 1281.
14. Syrengelas A D, Chen T T, Levy R. 1996. DNA immunization induces protective immunity against B-cell lymphoma. Nat Med. 2(9): 1038.
15. Biragyn A, Tani K, Grimm M C, Weeks S, Kwak L W. 1999. Genetic fusion of chemokines to a self tumor antigen induces protective, T-cell dependent antitumor immunity, Nat Biotechnol. 17(3): 253.
16. Bogen B. 1996. Peripheral T cell tolerance as a tumor escape mechanism: deletion of CD4+ T cells specific for a monoclonal immunoglobulin idiotype secreted by a plasmacytoma. Eur J Immunol. 26(11): 2671.
17. Rammensee H G, Falk K, Rotzschke O. 1993. Peptides naturally presented by MHC class I molecules. Annu Rev Immunol. 1993; 11: 213.
18. Rice J, King C A, Spellerberg M B, Fairweather N, Stevenson F K. 1999. Manipulation of pathogen-derived genes to influence antigen presentation via DNA vaccines. Vaccine. 17(23-24): 3030.
19. Mylin L M, Bonneau R H, Lippolis J D, Tevethia S S. 1995. Hierarchy among multiple H-2b-restricted cytotoxic T-lymphocyte epitopes within simian virus 40 T antigen. J Virol. 69(11): 6665.
20. Yewdell J W, Bennink J R. 1999. Immunodominance in major histocompatibility complex class I-restricted T lymphocyte responses. Annu Rev Immunol. 17: 51.
21. Umland T C, Wingert L M, Swaminathan S, Furey W F, Schmidt J J, Sax M. 1997. Related Articles, Protein, Structure Structure of the receptor binding fragment HC of tetanus neurotoxin. Nat Struct Biol. 4(10): 788.
22. Fairweather N F, Lyness V A. 1986. The complete nucleotide sequence of tetanus toxin. Nucleic Acids Res. 14(19): 7809.
23. Demotz S, Matricardi P, Lanzavecchia A, Corradin G. 1989. A novel and simple procedure for determining T cell epitopes in protein antigens. J Immunol Methods. 122(1): 67.
24. Panina-Bordignon P, Tan A, Termijtelen A, Demotz S, Corradin G, Lanzavecchia A. 1989. Universally immunogenic T cell epitopes: promiscuous binding to human MHC class II and promiscuous recognition by T cells. Eur J Immunol. 19(12): 2237.
25. Knapp M R, Liu C P, Newell N, Ward R B, Tucker P W, Strober S, Blattner F. 1982. Simultaneous expression of immunoglobulin mu and delta heavy chains by a cloned B-cell lymphoma: a single copy of the VH gene is shared by two adjacent CH genes. Proc Natl Acad Sci USA. 79(9): 2996.
26. Hawkins, R. E., G. Winter, T. J. Hamblin, F. K. Stevenson, and S. J. Russell. 1993. A genetic approach to idiotypic vaccination. J. Immunotherapy. 14: 273.
27. Kass, E., Schlom, J., Thompson, J., Guadagni, F., Graziano, P. and Greiner, J. W. 1999. Induction of protective host immunity to carcinoembryonic antigen (CEA), a self-antigen in CEA transgenic mice, by immunizing with a recombinant vaccinia-CEA virus. Cancer Research. 59: 676.
28. Thompson, J., Grunert, F. and Zimmerman, W. 1991. Carcinoembryonic antigen gene family: molecular biology and clinical perspectives. J. Clin. Lab. Anal. 5: 344
29. Elvin J, Cerundolo V, Elliott T, Townsend A. 1991. A quantitative assay of peptide-dependent class I assembly. Eur J Immunol. 21(9): 2025.
30. Cobbold S P, Jayasuriya A, Nash A, Prospero T D, Waldmann H. 1984. Therapy with monoclonal antibodies by elimination of T-cell subsets in vivo. Nature. 312(5994): 548.

31. Parker K C, Bednarek M A, Coligan J E. 1994. Scheme for ranking potential HLA-A2 binding peptides based on independent binding of individual peptide side-chains. J Immunol. 152(1): 163.
32. Andersen M H, Tan L, Sondergaard I, Zeuthen J, Elliott T, Haurum J S. 2000. Poor correspondence between predicted and experimental binding of peptides to class I MHC molecules. Tissue Antigens. 55(6): 519.
33. Widmann C, Romero P, Maryanski J L, Corradin G, Valmori D. 1992. T helper epitopes enhance the cytotoxic response of mice immunized with MHC class I-restricted malaria peptides. J Immunol Methods. 155(1): 95.
34. Maecker H T, Umetsu D T, DeKruyff R H, Levy S. 1998. Cytotoxic T cell responses to DNA vaccination: dependence on antigen presentation via class II MHC. J Immunol. 161(12): 6532.
35. Kass E, Schlom J, Thompson J, Guadagni F, Graziano P, Greiner J W. 1999. Induction of protective host immunity to carcinoembryonic antigen (CEA), a self-antigen in CEA transgenic mice, by immunizing with a recombinant vaccinia-CEA virus. Cancer Res. 59(3): 676.
36. Gurunathan S, Klinman D M, Seder R A. 2000. DNA vaccines: immunology, application, and optimization*. Annu Rev Immunol. 18: 927.
37. Zinkernagel R M, Pircher H P, Ohashi P, Oehen S, Odermatt B, Mak T, Arnheiter H, Burki K, Hengartner H. 1991. T and B cell tolerance and responses to viral antigens in transgenic mice: implications for the pathogenesis of autoimmune versus immunopathological disease. Immunol Rev. 122: 133.
38. Sandberg J K, Grufman P, Wolpert E Z, Franksson L, Chambers B J, Karre K. 1998. Superdominance among immunodominant H-2Kb-restricted epitopes and reversal by dendritic cell-mediated antigen delivery. J Immunol. 160(7): 3163.
39. Snyder H L, Bacik I, Yewdell J W, Behrens T W, Bennink J R. 1998. Promiscuous liberation of MHC-class I-binding peptides from the C termini of membrane and soluble proteins in the secretory pathway. Eur J Immunol. 28(4): 1339.
40. Suto, R., and P. K. Srivastava. 1995. A mechanism for the specific immunogenicity of heat shock protein chaperoned peptides. Science. 269: 1585.
41. Blobel, G. and Dobberstein, B. 1975. Transfer of proteins across cell membranes. J. Cell. Biol. 67: 835.
42. Cho B K, Palliser D, Guillen E, Wisniewski J, Young R A, Chen J, Eisen H N. 2000. A proposed mechanism for the induction of cytotoxic T lymphocyte production by heat shock fusion proteins. Immunity. 12(3): 263.

TABLE 1

Oligonucleotide primers used to assemble vaccine constructs (5'-3')

| | |
|---|---|
| FCf1 | TTTTAAGCTTGCCGCCACCATGGGTTGGAGC |
| FCr1 | AAAAGCGGCCGCTTAGTTACCCCAGAAGTCACGCAG |
| FCr2 | AAAGCGGCCGCTTACAGGTGGTTGAAGTACCAGTTAGAGTTACCCCAAAGTCACGCAG |
| FCr3 | AAAGCGGCCGCTTACAGACGTCGGTAGTAGATGTTCAGGTTACCCCAAAGTCACGCAG |
| FCr4 | AAAGCGGCCGCTTACAGGTAGGTTGTGTTCTGAGCCTCGTTACCCCAAAGTCACGCAG |

TABLE 1-continued

Oligonucleotide primers used to assemble vaccine constructs (5'-3')

| | |
|---|---|
| FCr5 | TTTGCGGCCGCTTACAGGTAGGTTGTGTTCTGAGCCTCGTCGTTGGTCAACCTTCATCGGT |
| PCMVf1 | CTATATAAGCAGAGCTCT |
| BCL₁r1 | GGTGAAGTTGTTGAAGGAGTGCACACCTGTAGCTGT |
| P30f1 | ACAGGTGTGCACTCCTTCAACAACTTCACCGTTAGC |
| P30r1 | AAAGCGGCCGCTTACAGGTGGTTGAAGTACCAGTTAGATTCCAGGTGGAAGCAGAAAC |
| P30r2 | AAAGCGGCCGCTTACAGACGTCGGTAGTAGATGTTCAGTTCCAGGTGGAAGCAGAAAC |

Restriction enzyme sites are underlined.

Restrictions enzymes sites are underlined.
FCf1=SEQ ID NO: 9
FCR1=SEQ ID NO: 10
FCr2=SEQ ID NO: 11
FCr3=SEQ ID NO: 12
FCr4=SEQ ID NO: 13
FCr5=SEQ ID NO: 14
PCMVf1=SEQ ID NO: 15
BCL₁r1=SEQ ID NO: 16
P30f1=SEQ ID NO: 17
P30r1=SEQ ID NO: 18
P304r2=SEQ ID NO: 19

The amino acid sequence (SEQ ID NO: 20) of tetanus toxin is:

1 MPITINNFRY SDPVNNDTII MMEPPYCKGL DIYYKAFKIT DRIWIVPERY EFGTKPEDFN
61 PPSSLIEGAS EYYDPNYLRT DSDKDRFLQT MVKLFNRIKN NVAGEALLDK IINAIPYLGN
121 SYSLLDKFDT NSNSVSFNLL EQDPSGATTK SAMLTNLIIF GPGPVLNKNE VRGIVLRVDN
181 KNYFPCRDGF GSIMQMAFCP EYVPTFDNVI ENITSLTIGK SKYFQDPALL LMHELIHVLH
241 GLYGMQVSSH EIIPSKQEIY MQHTYPISAE ELFTFGGQDA NLISIDIKND LYEKTLNDYK
301 AIANKLSQVT SCNDPNIDID SYKQIYQQKY QFDKDSNGQY IVNEDKFQIL YNSIMYGFTE
361 IELGKKFNIK TRLSYFSMNH DPVKIPNLLD DTIYNDTEGF NIESKDLKSE YKGQNMRVNT
421 NAFRNVDGSG LVSKLIGLCK KIIPPTNIRE NLYNRTASLT DLGGELCIKI KNEDLTFIAE
481 KNSFSEEPFQ DEIVSYNTKN KPLNFNYSLD KIIVDYNLQS KITLPNDRTT PVTKGIPYAP
541 EYKSNAASTI EIHNIDDNTI YQYLYAQKSP TTLQRITMTN SVDDALINST KIYSYFPSVI
601 SKVNQGAQGI LFLQWVRDII DDFTNESSQK TTIDKISDVS TIVPYIGPAL NIVKQGYEGN
661 FIGALETTGV VLLLEYIPEI TLPVIAALSI AESSTQKEKI IKTIDNFLEK RYEKWIEVYK
721 LVKAKWLGTV NTQFQKRSYQ MYRSLEYQVD AIKKIIDYEY KIYSGPDKEQ IADEINNLKN
781 KLEEKANKAM ININIFMRES SRSFLVNQMI NEAKKQLLEF DTQSKNILMQ YIKANSKFIG.
841 ITELKKLESK INKVFSTPIP FSYSKNLDCW VDNEEDIDVI LKKSTILNLD INNDIISDIS
901 GFNSSVITYP DAQLVPGING KAIHLVNNES SEVIVHKAMD IEYNDMFNNF TVSFWLRVPK

961  VSASHLEQYG TNEYSIISSM KKHSLSIGSG WSVSLKGNNL IWTLKDSAGE VRQITFRDLP
1021 DKFNAYLANK WVFITITNDR LSSANLYING VLMGSAEITG LGAIREDNNI TLKLDRCNNN
1081 NQYVSIDKFR IFCKALNPKE IEKLYTSYLS ITFLRDFWGN PLRYDTEYYL IPVASSSKDV
1141 QLKNITDYMY LTNAPSYTNG KLNIYYRRLY NGLKFIIKRY TPNNEIDSFV KSGDFIKLYV
1201 SYNNNEHIVG YPKDGNAFNN LDRILRVGYN APGIPLYKKM EAVKLRDLKT YSVQLKLYDD
1261 KNASLGLVGT HNGQIGNDPN RDILIASNWY FNHLKDKILG CDWYFVPTDE GWTND

---

The invention claimed is:

1. A nucleic acid construct for delivery into living cells in vivo to induce an immune response in a patient to a disease peptide antigen; the construct directing the expression of a fusion protein consisting of the disease peptide antigen and the naturally occurring first domain of fragment C (FrC) of tetanus toxin; wherein said first domain consists of amino acids 865 to 1120 of tetanus toxin.

2. The nucleic acid construct according to claim 1 wherein the disease peptide antigen is a tumour antigen.

3. The nucleic acid construct according to claim 1 wherein said disease peptide antigen is an idiotypic determinant.

4. The nucleic acid construct according to claim 3 wherein the idiotypic determinant is a single chain variable fragment (scFv fragment).

5. The nucleic acid construct according to claim 1 wherein the disease peptide antigen has between 5 and 30 amino acids.

6. The nucleic acid construct according to claim 5 wherein said disease peptide antigen has between 8 and 25 amino acids.

7. A nucleic acid construct for delivery into living cells in vivo to induce an immune response in a patient to a disease peptide antigen; the construct directing the expression of a fusion protein consisting of a leader sequence which is capable of directing the fusion protein to endoplasmic reticulum, the disease peptide antigen and the naturally occurring first domain of fragment C (FrC) of tetanus toxin; wherein said first domain consists of amino acids 865 to 1120 of tetanus toxin.

8. A nucleic acid expression vector comprising the nucleic acid construct according to claim 1.

9. An isolated host cell comprising the nucleic acid construct according to claim 1.

10. A nucleic acid vaccine for inducing an immune response in a patient, comprising the nucleic acid construct according to claim 1.

11. A method of producing a nucleic acid construct for inducing an immune response in a patient, said method comprising:
    (a) identifying a nucleic acid sequence encoding a disease peptide antigen comprising epitopes characteristic of the disease;
    (b) cloning the nucleic acid sequence encoding the disease peptide antigen; and
    (c) introducing the cloned nucleic acid sequence into a vector, which vector allows for the disease peptide antigen to be expressed as a fusion protein with the naturally occurring first domain of FrC from tetanus toxin; wherein said first domain consists of amino acids 865 to 1120 of tetanus toxin.

12. The method according to claim 11 wherein the vector further comprises a nucleotide sequence encoding a leader sequence for association with the encoded fusion protein.

13. The method according to claim 11 further comprising the step of isolating a nucleic acid construct from the vector, said nucleic acid construct directing the expression of the fusion protein consisting of the first domain of FrC from tetanus toxin and the disease peptide antigen.

14. The method according to claim 13 further comprising the step of preparing a vaccine composition comprising the nucleic acid construct.

15. A method of inducing an immune response to a disease peptide antigen in a patient, said method comprising administering to the patient the nucleic acid construct according to claim 1.

16. The method according to claim 15 wherein the nucleic acid construct is administered directly into muscle cells of the patient.

17. A composition comprising the nucleic acid construct according to claim 1 and a physiologically acceptable diluent or carrier.

18. A composition comprising the nucleic acid expression vector according to claim 8 and a physiologically acceptable diluent or carrier.

19. The composition according to claim 18 wherein the vector further directs the expression of immunomodulatory polypeptides.

20. The nucleic acid construct according to claim 2 wherein said disease peptide antigen is an idiotypic determinant.

21. The nucleic acid construct according to claim 20 wherein the idiotypic determinant is a scFv fragment.

22. The nucleic acid construct according to claim 2 wherein the disease peptide antigen has between 5 and 30 amino acids.

23. The nucleic acid construct according to claim 22 wherein said disease peptide antigen has between 8 and 25 amino acids.

24. A nucleic acid construct for delivery into living cells in vivo to induce an immune response in a patient to a disease peptide antigen; the construct directing the expression of a fusion protein consisting of a leader sequence which is capable of directing the fusion protein to endoplasmic reticulum, the disease peptide antigen and the naturally occurring first domain of fragment C (FrC) of tetanus toxin; wherein said first domain consists of amino acids 865 to 1120 of tetanus toxin and wherein the disease peptide antigen is a tumour antigen.

25. A nucleic acid expression vector comprising the nucleic acid construct according to claim 2.

26. An isolated host cell comprising the nucleic acid construct according to claim 2.

27. An isolated host cell comprising the nucleic acid expression vector according to claim 8.

28. An isolated host cell comprising the nucleic acid expression vector according to claim 25.

29. A nucleic acid vaccine for inducing an immune response in a patient, comprising the nucleic acid construct according to claim 2.

30. A nucleic acid vaccine for inducing an immune response in a patient, comprising the nucleic acid expression vector according to claim 8.

31. A nucleic acid vaccine for inducing an immune response in a patient, comprising the nucleic acid expression vector according to claim 25.

32. The method according to claim 12 further comprising the step of isolating a nucleic acid construct from the vector, said nucleic acid construct directing the expression of the fusion protein consisting of the first domain of FrC from tetanus toxin and the disease peptide antigen.

33. The method according to claim 32 further comprising the step of preparing a vaccine composition comprising the nucleic acid construct.

34. A method of inducing an immune response to a disease peptide antigen in a patient, said method comprising administering to the patient the nucleic acid construct according to claim 2.

35. The method according to claim 34 wherein the nucleic acid construct is administered directly into muscle cells of the patient.

36. A method of inducing an immune response to a disease peptide antigen in a patient, said method comprising administering to the patient the nucleic acid expression vector according to claim 8.

37. The method according to claim 36 wherein the nucleic acid expression vector is administered directly into muscle cells of the patient.

38. A method of inducing an immune response to a disease peptide antigen in a patient, said method comprising administering to the patient the nucleic acid expression vector according to claim 25.

39. The method according to claim 38 wherein the nucleic acid expression vector is administered directly into muscle cells of the patient.

40. A composition comprising the nucleic acid construct according to claim 2 and a physiologically acceptable diluent or carrier.

41. A composition comprising the nucleic acid expression vector according to claim 25 and a physiologically acceptable diluent or carrier.

42. The composition according to claim 41 wherein the vector further directs the expression of immunomodulatory polypeptides.

* * * * *